(12) United States Patent
Deng et al.

(10) Patent No.: US 7,582,764 B2
(45) Date of Patent: Sep. 1, 2009

(54) ASYMMETRIC CARBON-CARBON-BOND-FORMING REACTIONS CATALYZED BY BIFUNCTIONAL CINCHONA ALKALOIDS

(75) Inventors: Li Deng, Newton, MA (US); Hongming Li, Waltham, MA (US); Yi Wang, Waltham, MA (US); Fanghui Wu, Waltham, MA (US)

(73) Assignee: Brandeis University, Waltham, MA (US)

( * ) Notice: Subject to any disclaimer, the term of this patent is extended or adjusted under 35 U.S.C. 154(b) by 136 days.

(21) Appl. No.: 11/442,742

(22) Filed: May 26, 2006

(65) Prior Publication Data

US 2007/0083049 A1 Apr. 12, 2007

Related U.S. Application Data

(63) Continuation-in-part of application No. 11/140,574, filed on May 27, 2005, now Pat. No. 7,312,335.

(60) Provisional application No. 60/576,754, filed on Jun. 3, 2004, provisional application No. 60/592,500, filed on Jul. 30, 2004, provisional application No. 60/742,102, filed on Dec. 2, 2005.

(51) Int. Cl.
*C07D 453/04* (2006.01)
(52) U.S. Cl. ...................................... 546/134
(58) Field of Classification Search .................. 546/134, 546/135, 136
See application file for complete search history.

(56) References Cited

U.S. PATENT DOCUMENTS

| 1,720,462 A | 7/1929 | Blagden |
| 2,072,004 A | 2/1937 | Lutz |
| 2,377,814 A | 6/1945 | Schnider |

FOREIGN PATENT DOCUMENTS

| WO | WO-02/05953 A2 | 1/2002 |
| WO | WO-03/011799 A1 | 2/2003 |
| WO | WO-03/018549 A2 | 3/2003 |

OTHER PUBLICATIONS

Taggi et al., Journal of the American Chemical Society (2000),122(32), 7831-7832.*
Blaser et al., Journal of the American Chemical Society (2000),122(51), 12675-12682.*
Brunner et al., European Journal of Organic Chemistry (2000), (11), 2119-2133.*
Brunner et al., Tetrahedron: Asymmetry (2000), 11(7), 1501-1512.*
Brunner et al., Tetrahedron: Asymmetry (1995), 6(7), 1699-702.*
Li, H. et al., "Stereocontrolled Creation of Adjacent Quaternary and Tertiary Stereocenters by a Catalytic Conjugate Addition", XP-002344994, Angew Chem. Int. Ed. 44: 105-108 (2005).

Ma, D. et al., "Diastereoselective Henry reactions of N,N-dibenzyl χ-amino aldehydes with nitromethane catalyzed by enantiopure guanidines", XP-002399848 Tetrahedron Letters 43: 9401-9403 (2002).
Rogers, L. M-A. et al., "Enantioselective decarboxylation-reprotonation of an χ-amino malonte derivative as a route to optically enriched cyclic χ-amino acid", XP-002399840 Tetrahedron Letters 44: 3047-3050 (2003).
Brunner, H. et al., "α-Amino Acid Derivatives by Enantioselective Decarboxylation", XP-002399850 Eur. J. Org. Chem. 2854-2862 (2003).
Brunner, H. et al., "Asymmetric Catalysis, 131 Naproxen Derivatives by Enantioselective Decarboxylation", XP-002399851 Eur. J. Org. Chem. 2119-2133 (2000).
Vakulya, B. et al., "Highly Enantioselective Conjugate Addition of Nitromethane to Chalcones Using Bifunctional Cinchona Organocatalysts", XP002399852 Organic Letters 7(10): 1967-1969 (2005).
Li, B.-J. et al., "Asymmetic Michael Addition of Arylthiols to α,β-Unsaturated Carbonyl Compounds Catalyzed by Bifunctional Organocatalysts", XP-002399853 Synlett 4: 0603-0606 (2005).
McCooey, S. et al., "Urea- and Thiourea-Substituted Chinchona Alkaloid Derivatives as Highly Efficient Bifunctional Organocatalysts for the Asymmetric Addtion of Malonate Nitroalkenes: Inversion of Configuration at C9 Dramatically Improves Catalyst Performance" XP-002399854 Angew Chem. Int. Ed. 44: 6367-6370 (2005).

(Continued)

*Primary Examiner*—D. Margaret Seaman
*Assistant Examiner*—Niloofar Rahmani
(74) *Attorney, Agent, or Firm*—Dana M. Gordon; Foley Hoag LLP

(57) ABSTRACT

One aspect of the present invention relates to quinine-based and quinidine-based catalysts. In certain embodiments, the quinine-based and quinidine-based catalysts contain a hydroxy group at the 6' position. In certain embodiments, the quinine-based and quinidine-based catalysts contain an O-aryl group or an O-aroyl group at the C9 position. In certain embodiments, the quinine-based and quinidine-based catalysts contain an optionally substituted O-diazene group or an optionally substituted O-benzoyl group at the C9 position. In certain embodiments, the quinine-based and quinidine-based catalysts contain a thiourea at the C9 position. In certain embodiments, the quinine-based and quinidine-based catalysts contain an NH(=S)NH-aryl group at the C9 position. Another aspect of the present invention relates to a method of preparing a chiral, non-racemic compound from a prochiral electron-deficient alkene or prochiral imine, comprising the step of: reacting a prochiral alkene or imine with a nucleophile in the presence of a catalyst; thereby producing a chiral, non-racemic compound; wherein said catalyst is a derivatized quinine or quinidine. In certain embodiments, the nucleophile is a malonate or β-ketoester. In certain embodiments the nucleophile is an alkyl or aryl or aralkyl 2-cyano-2-alkylacetate. In certain embodiments the nucleophile is an alkyl or aryl or aralkyl 2-cyano-2-alkylacetate.

Another aspect of the present invention relates to a method of kinetic resolution, comprising the step of: reacting a racemic aldehyde or racemic ketone with a nucleophile in the presence of a derivatized quinine or quinidine, thereby producing a non-racemic, chiral compound. In certain embodiments, the kinetic resolution is dynamic.

20 Claims, 15 Drawing Sheets

OTHER PUBLICATIONS

Ye, J. et al., Enantioselective Organocatalytic Michael addition of malonate esters to nitro olefins using bifunctional cinchonine derivatives XP-002399855 Chem. Commun. 4481-4483 (2005).

Tillman, A. L. et al., "Direct enantio- and diastereoselective Mannich reactions of malonate and β-keto esters with N-Boc and N—Cbz aldimines catalysed by a bifunctional cinchonine derivative", XP-002399856 Chem. Commun. 1191-1193 (2006).

Song, J. et al., The Mannich Reaction of Malonates with Simple Imines Catalyzed by Bifunctional Cinchona Alkaloids: Enantioselective Synthesis of β-Amino Acids, XP-002399857 J. Am. Chem. Soc. 128: 6048-6049 (2006).

Liu, T.Y. et al., "Enantioselective construction of Quaternary carbon centre catalysed by bifunctional organocatalyst", XP-002399858 Org. Biomol. Chem. 4: 2097-2099 (2006).

Li, H. et al., "Organocatalytic enantioselective Michael addition of thioacetic acid to enones", XP-002399859 Tetrahedron Letters 47: 3145-3148 (2006).

Partial International Search Report based on PCT/US06/020324.

Barnes, D. M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", J. Am. Chem. Soc., 124:13097-13105 (2002).

Berner, O. M. et al., "Asymmetric Michael Additions to Nitroalkenes", Eur. J. Org. Chem., 1877-1894 (2002).

Brunner, H. et al., "Asymmetric Catalysis, CIII[1]: Enantioselective Michael Addition of 1,3-Dicarbonyl Compounds to Conjugated Nitroalkenes", Monatshefte für Chemie, 127:1063-1072 (1996).

Calter, M. A., "Catalytic, Asymmetric Dimerization of Methylketene", J. Org. Chem., 61:8006-8007 (1996).

Chen, Y, et al., "Asymmetric Alcoholysis of Cyclic Anhydrides", Chem. Rev., 103:2965-2983 (2003).

Cortez, G. S. et al., "Bicyclic β-Lactones via Intramolecular NCAL Reactions with Cinchona Alkaloids: Effect of the C9-Substituent on Enantioselectivity and Catalyst Conformation", Synthesis, 11:1731-1736 (2001).

Cortez, G. S. et al., "Intramolecular, Nucleophile-Catalyzed Aldol-Lactonization (NCAL) Reactions: Catalytic, Asymmetric Synthesis of Bicyclic β-Lactones", J. Am. Chem. Soc., 123:7945-7946 (2001).

France, S. et al., "Nucleophilic Chiral Amines as Catalysts in Asymmetric Synthesis", Chem. Rev., 103:2985-3012 (2003).

Gröger, H., "The Development of New Monometallic Bifunctional Catalysts with Lewis acid and Lewis Base Properties, and their Application in Asymmetric Cyanation Reactions", Chem. Eur. J., 7(24):5247-5251 (2001).

Heimstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis", J. Am. Chem. Soc., 103:417-430 (1981).

Hiemstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis", J. Am. Chem. Soc., 103:417-430 (1981).

Iwabuchi, Y. et al., "Chiral Amine-Catalyzed Asymmetric Baylis-Hillman Reaction: A Reliable Route to Highly Enantiomerically Enriched (a-Methylene-β-hydroxy)esters", J. Am. Chem. Soc., 121:10219-10220 (1999).

Ji, J. et al., "Catalytic Enantioselective Conjugate Addition of 1,3-Dicarbonyl Compounds to Nitroalkenes", J. Am. Chem. Soc., 121:10215-10216 (1999).

Kawahara, S. et al., "β-Isocupreidine-Catalyzed Asymmetric Baylis-Hillman Reaction of Imines", Organic Letters, 5(17):3103-3105 (2003).

Li, H. et al., "Catalytic Enantioselective C-C Bond Forming Conjugate Additional with Vinyl Sulfones", J. Am. Chem. Soc., 127:8948-8949 (2005).

Li, H. et al., "Highly Enantioselective Conjugate Addition of Malonate and β-Ketoester to Nitroalkenes: Asymmetric C-C Bond Formation with New Bifunctional Organic Catalysts Based on Cinchona Alkaloids", J. Am. Chem. Soc., 126:9906-9907 (2004).

Li, H. et al., "Stereocontrolled Creation of Adjacent Quaternary and Tertiary Stereocenters by a Catalytic Conjugate Addition", Angew. Chem. Int. Ed., 44:105-108 (2005).

List, B., "Asymmetric Aminocatalysis", Synlett, 11:1675-1686 (2001).

Liu, X. et al., "Highly Enantioselective Amination of a-Substituted a-Cyanoacetates with Chiral Catalysts Accessible from Both Quinine and Quinidine", Organic Letters, 7(2):167-169 (2005).

List, B., "Proline-catalyzed asymmetric reactions", Tetrahedron, 58:5573-5590 (2002).

Marcelli, T. et al., "Cinchona Derivatives as Bifunctional Organocatalysts for the Direct Asymmetric Nitroaldol (Henry) Reaction", Synlett., 18:2817-2819 (2005).

Okino, T. et al., "Enantioselective Michael Reaction of Malonates to Nitroolefins Catalyzed by Bifunctional Organocatalysts", J. Am. Chem. Soc., 125:12672-12673 (2003).

Rogers, L. M. A. et al., "Enantioselective decarboxylation-reprotonation of an a-amino malonate derivative as a route to optically enriched cyclic λ-amino acid", Tetrahedron Letters, 44:3047-3050 (2003).

Shibasaki, M. et al., "Asymmetric Catalysis with Heterobimetallic Compounds", Angew. Chem. Int. Ed. Enql., 36:1236-1256 (1997).

Shibasaki, M. et al., "Lanthanide Complexes in Multifunctional Asymmetric Catalysis", Chem. Rev., 102:2187-2209 (2002).

Sibi, M. P. et al., "Enantioselective Conjugate Additions", Tetrahedron, 56:8033-8061 (2000).

Suzko, J. et al., "B-Isoquinine and niquine", Roczniki Chemii, 5:358-385 (1925).

Taggi, A. E. et al., "Catalytic, Asymmetric Synthesis of β-Lactams", J. Am. Chem. Soc., 122:7831-7832 (2000).

Tian, S-K, et al., "Asymmetric Organic Catalysis with Modified Cinchona Alkaloids", Acc. Chem. Res. (abstract), Dec. 10 2003.

Wack, H. et al., "Catalytic, Asymmetric a-Halogenation", J. Am. Chem. Soc., 123:1531-1532 (2001).

Wynberg, H., "Asymmetric Catalysts by Alkaloids", Top. Stereochem., 16:87-129 (1986).

Czerwenka, C. et al., "Direct High-Performance Liquid Chromatographic Separation of Peptide Enantiomers: Study on Chiral Recognition by Systematic Evaluation of the Influence of Structural Features of the Chiral Selectors on Enantioselectivity," Analytical Chemistry 74:5658-5666 (2002).

Deady, L.W. et al., "A Cinchonidine Derivative for Photoaffinity Labelling of Proteins," Journal of Labelled Compounds and Radiopharmaceuticals 43:977-981 (2002).

Cowman, A.F. et al., "Synthesis and Activity of Some Antimalarial Bisquinolinemethanols," Australian Journal of Chemistry 50:1091-1096 (1997).

Dorwald, F.Z. et al., "Side Reactions in Organic Synthesis," Wiley: VCH, Weinheim p. IX of Preface (2005).

Dorwald, F.Z. et al., "Side Reactions in Organic Synthesis," Wiley: VCH, Weinheim pp. 1-15 (2005).

\* cited by examiner

Figure 4
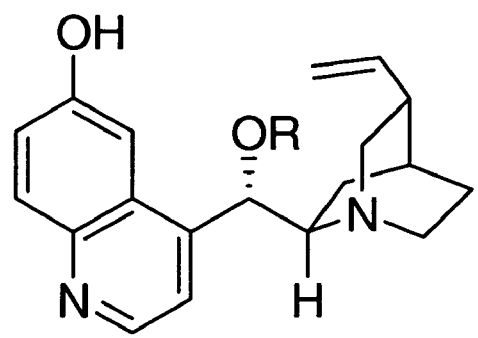
R = PHN, Qd-1a
R = Bn, Qd-1b
R = H, Qd-1c
R = Ac, Qd-1d
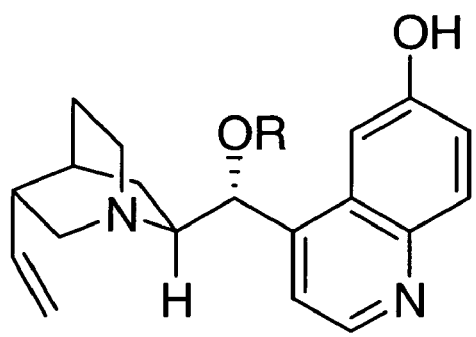
R = PHN, Q-1a
PHN =

| entry | catalyst | toluene (mL) | time (hr) | conv.$^b$ (%) | d.r.$^b$ | ee$^c$ of major isomer (%) |
|---|---|---|---|---|---|---|
| 1 | (DHQD)$_2$PHAL | 0.05 | 20 | 82 | 1.1 | 13 |
| 2 | (DHQD)$_2$AQN | 0.05 | 20 | 36 | 1.2 | 23 |
| 3 | (DHQD)$_2$PRY | 0.05 | 20 | 95 | 1.2 | 33 |
| 4 | DHQD-PHN | 0.05 | 20 | 74 | 1.1 | 13 |
| 5 | Qd-1c | 0.05 | 20 | 90 | 1.6 | 16 |
| 6 | Qd-1b | 0.05 | 20 | 95 | 2.3 | 57 |
| 7 | Qd-1a | 0.05 | 20 | 93 | 3.1 | 75 |
| 8 | Qd-1a | 0.50 | 60 | 71 | 5.0 | 90 |
| 9 | Qd-1a$^d$ | 0.50 | 60 | 99 | 7.0 | 91 |

| Entry | Michael donor | Catalyst loading (mol%) | Product | Time (hr) | Yield[b] (%) | d.r.[c] | ee[d] of major isomer (%) |
|---|---|---|---|---|---|---|---|
| 1 | 3a | 20 | 4a | 48(96) | 93(89) | 7:1(5:1) | 91(85) |
| 2 | n = 1, 3b | 10 | 4b | 4(7) | 95(95) | 20:1(20:1) | 96[f](93) |
| 3 | n = 2, 3c | 20 | 4c | 72(96[e]) | 87(92) | 11:1(8:1) | 91(87) |
| 4 | n = 3, 3d | 10 | 4d | 24(72) | 88(92) | 25:1(25:1) | 95(94) |
| 5 | 3e | 20 | 4e | 48(48) | 71(74) | 9:1(8:1) | 93(92) |
| 6 | X = H, 3f | 10 | 4f | 24(48) | 94(91) | 17:1(17:1) | 98(98) |
| 7 | X = Cl, 3g | 10 | 4g | 36(24) | 81(82) | 20:1(16:1) | 99[f](98) |
| 8 | 3h | 20 | 4h | 48(48) | 75(78) | 20:1(17:1) | 98(97) |

Figure 7
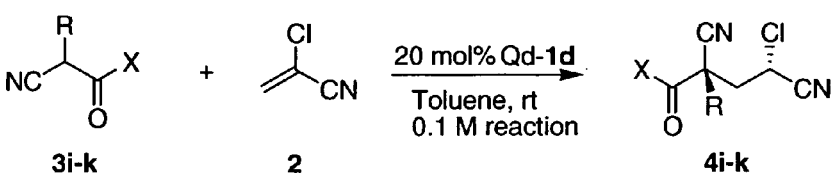
| Entry | Michael donor | | Catalyst | Product | Time (hr) | Yield[b] (%) | d.r.[c] | ee[d] of major isomer (%) |
|---|---|---|---|---|---|---|---|---|
| 1 | 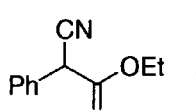 | 3i | Qd-1a | 4i | 96 | 99[e] | 2:1 | 79 |
| 2 | | | Qd-1d | 4i | 96[f] | 85 | 4:1 | 88 |
| 3 | 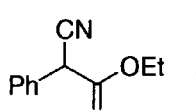 | 3j | Qd-1d | 4j | 20 | 12[e] | 5:1 | 85 |
| 4 | 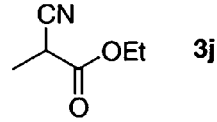 | 3k | Qd-1d | 4k | 96 | 71 | 10:1 | 93[h] |
| 5 | 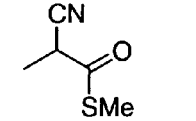 | 3l | Qd-1d | 4l | 96 | 60[g] | 7:1 | 89 |

Figure 8
catalyst structure:
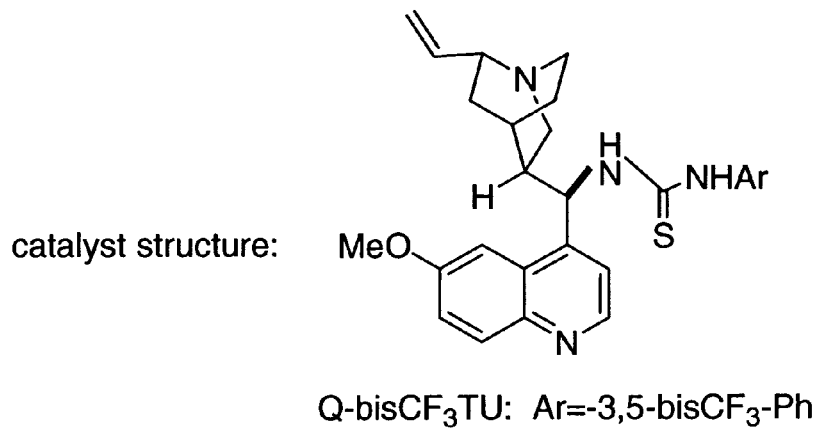
Q-bisCF$_3$TU: Ar=-3,5-bisCF$_3$-Ph
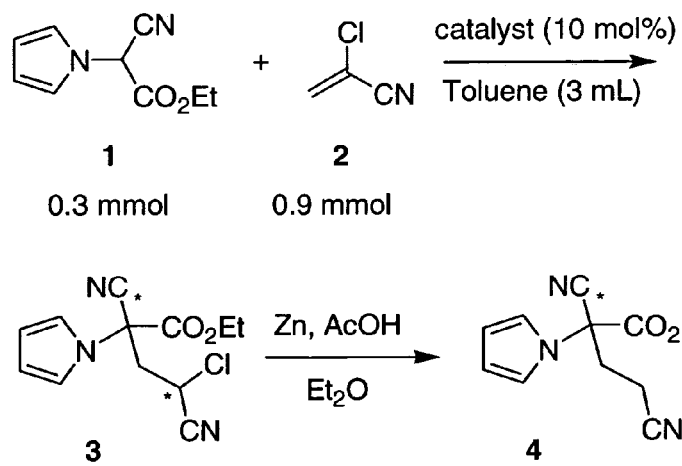
| Entry | Temp./C | Time/hr | Yield of 3/% | ee of 4/% |
|-------|---------|---------|--------------|-----------|
| 1 | 23 | <15 | 100 | 87 |
| 2 | -24 | 48 | 100 | 92 |

| entry | R | X | T(°C) | time(h) | yield(%)[b] | ee(%)[c] |
|---|---|---|---|---|---|---|
| 1 | Ph | OEt | r.t. | 96(96) | 95(93) | 89(90) |
| 2 | | | 50 | 48 | 97 | 85 |
| 3 | p-F-Ph | OEt | r.t. | 120(72) | 84(87) | 88(90) |
| 4 | p-Cl-Ph | OEt | r.t. | 52(52) | 96(96) | 88(89) |
| 5 | m-Cl-Ph | OEt | r.t. | 52 | 99 | 88 |
| 6 | p-Br-Ph | OEt | r.t. | 72(72) | 89(82) | 89(89) |
| 7 | p-Me-Ph | OEt | r.t. | 114 | 92 | 90 |
| 8 | | | 50 | 72 | 98 | 86 |
| 9 | p-MeO-Ph | OEt | r.t. | 117 | 85 | 90 |
| 10 | | | 50 | 72 | 97 | 87 |
| 11 | 2-Naphthalyl | OEt | r.t. | 90 | 89 | 89 |
| 12 | Allyl | SMe | r.t. | 88 | 82 | 91 |
| 13 | Methyl | SMe | r.t. | 72 | 80 | 93[d] |
| 14 | p-Cl-Ph | OtBu | r.t. | 64 | 82 | 88 |
| 15 | (indanone-CN-CH2CN) | | r.t. | 12 | 100 | 93[d] |
| 16 | (tetralone-CN-CH2CN) | | r.t. | 36 | 92 | 94 |

Figure 10

| entry | substrates | time(h) | yield(%)[b] | d.r.[c] | ee(%)[d] |
|---|---|---|---|---|---|
| 1 | indanone-CN | 1 | 99 | 10:1 | 97[e] |
| 2 | tetralone-CN | 11 | 94 | 16:1 | 99 |
| 3 | benzosuberone-CN | 10 | 98 | 9:1 | 97 |
| 4[f] | Ph-C(CN)(COOEt) | 12(11) | 98(99) | 15:1(16:1) | 95(95) |
| 5[g] | Ph-C(CN)(COOEt) | 20 | 98 | 25:1 | 97 |
| 6 | 4-F-C6H4-C(CN)(COOEt) | 11 | 98 | 13:1 | 95 |
| 7 | 4-Cl-C6H4-C(CN)(COOEt) | 12 | 98 | 13:1 | 94 |
| 8 | 4-Br-C6H4-C(CN)(COOEt) | 12 | 98 | 12:1 | 95 |
| 9 | 4-Me-C6H4-C(CN)(COOEt) | 12 | 100 | 14:1 | 95 |
| 10 | 4-MeO-C6H4-C(CN)(COOEt) | 12 | 99 | 13:1 | 95 |
| 11 | 2-naphthyl-C(CN)(COOEt) | 12 | 100 | 14:1 | 95 |
| 12 | Me-C(CN)(COSMe) | 12 | 98 | 9:1 | 96[e] |
| 13 | allyl-C(CN)(COSMe) | 14 | 99 | 9:1 | 95 |
| 14 | Me-C(CN)(COOCH2CF3) | 48 | 98 | 8:1 | 83 |
| 15 | allyl-C(CN)(COOEt) | 120 | 97 | 12:1 | 93 |

Figure 11
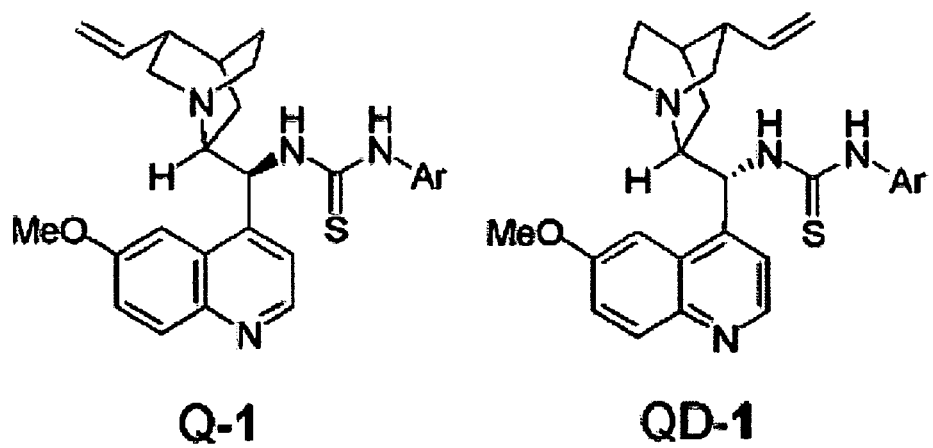
1a Ar = 4-*t*-Bu-Ph-; 1b Ar = 2-*i*-Pr-Ph-;
1c Ar = Ph-; 1d Ar = 3,5-*bis*CF₃Ph-
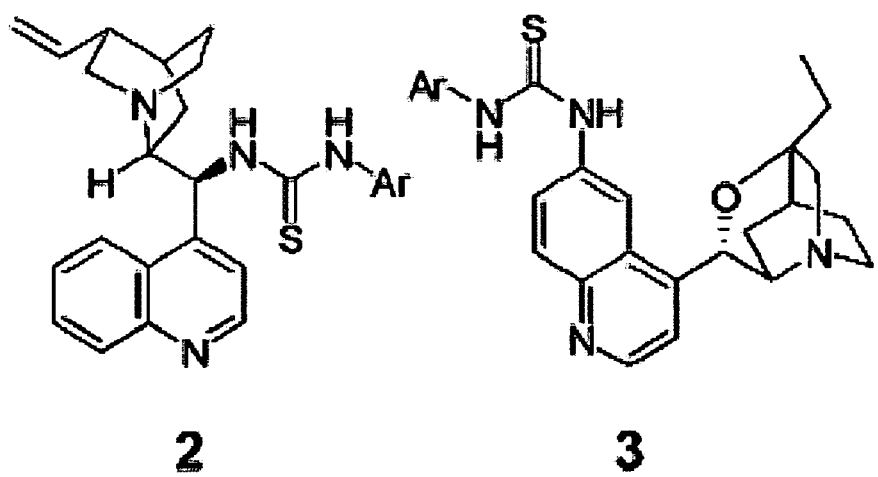
2,3: Ar = 3,5-*bis*CF₃Ph- Manzacidin A, 13

Figure 13

| entry | cat.[b] | temp (°C) | solvent | conv./%[c] | ee/%[d] |
|---|---|---|---|---|---|
| 1 | Q-1a | RT | CH$_2$Cl$_2$ | >98 | 57 |
| 2 | Q-1b | RT | CH$_2$Cl$_2$ | >98 | 43 |
| 3 | Q-1c | RT | CH$_2$Cl$_2$ | >98 | 62 |
| 4 | Q-1d | RT | CH$_2$Cl$_2$ | >98 | 77 |
| 5 | QD-1d | RT | CH$_2$Cl$_2$ | >98 | -74 |
| 6 | 2 | RT | CH$_2$Cl$_2$ | >98 | 65 |
| 7 | 3 | RT | CH$_2$Cl$_2$ | >98 | 72 |
| 8 | Q-1d | RT | CH$_3$CN | >98 | 83 |
| 9 | Q-1d | RT | Acetone | >98 | 77 |
| 10 | Q-1d | -20 | CH$_2$Cl$_2$ | >98 | 80 |
| 11 | Q-1d | -20 | CH$_3$CN | >98 | 74 |
| 12 | Q-1d | -20 | Acetone | >98 | 85 |
| 13[e] | Q-1d | -60 | Acetone | >98 | 93 |

Figure 14

$$\underset{4}{\overset{NBoc}{\underset{H}{\overset{\|}{R}}}} + CH_2(COOR')_2 \xrightarrow[\text{5 a: R'=Me; b: R'=Bn; c: R'=Allyl}]{QD\text{-}1d\ (Q\text{-}1d)\ (20\ mol\%)} \underset{6}{\overset{NHBoc}{\underset{COOR'}{\overset{\|}{R^*}}}}\overset{COOR'}{}$$

| entry | | R | 5 | yield/%[b] | ee/%[c,d] |
|---|---|---|---|---|---|
| 1 | 4B | 2-Me-Ph- | 5b | 98(96) | 99(95) |
| 2 | 4C | 3-Me-Ph- | 5b | 99(99) | 98(97) |
| 3 | 4D | 4-Me-Ph- | 5b | 92(96) | 97(92) |
| 4 | 4E | 4-F-Ph- | 5b | 99(98) | 99(94) |
| 5 | 4F | 4-Cl-Ph | 5b | 98(97) | 99(91) |
| 6 | 4G | 4-CF$_3$-Ph- | 5b | 81(82) | 97(93) |
| 7 | 4H | 2-furyl- | 5b | 99(99) | 97(96) |
| 8 | 4I | 2-thienyl- | 5b | 95(96) | 97(88) |
| 9 | 4J | 4-OMe-Ph- | 5b | 98(97) | 97(93) |
| 10[e] | 4J | 4-OMe-Ph- | 5b | 91 | 96 |
| 11 | 4K | 3,4-OCH$_2$O-Ph- | 5b | 99(99) | 98(94) |
| 12 | 4L | 3-vinyl-Ph- | 5c | 96(99) | 96(95) |
| 13[f] | 4M | CH$_3$CH$_2$- | 5b | 63 | 89 |
| 14[f] | 4N | CH$_3$(CH$_2$)$_2$CH$_2$- | 5b | 64 | 92 |
| 15[f] | 4O | cyclohexyl- | 5b | 55 | 88 |
| 16 | 4A | Ph- | 5a | 90(91) | 97(93) |
| 17 | 4A | Ph- | 5b | 99(99) | 96(94) |
| 18 | 4A | Ph- | 5c | 91(86) | 98(92) |

[A]

[B]

ASYMMETRIC CARBON-CARBON-BOND-FORMING REACTIONS CATALYZED BY BIFUNCTIONAL CINCHONA ALKALOIDS

RELATED APPLICATIONS

This application is a continuation-in-part of U.S. patent application Ser. No. 11/140,574, filed on May 27, 2005; which claims priority to U.S. provisional patent application Ser. No. 60/576,754, filed on Jun. 3, 2004; and U.S. provisional patent application Ser. No. 60/592,500, filed on Jul. 30, 2004; all of which are expressly incorporated by reference. In addition, this application claims priority to U.S. provisional patent application Ser. No. 60/742,102, filed on Dec. 2, 2005; which is expressly incorporated by reference.

GOVERNMENT SUPPORT

The invention was made with support provided by the National Institutes of Health (GM-61591); therefore, the government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

Enantiomerically pure materials may be obtained by asymmetric conjugate addition of a nucleophile to an electron-poor alkene. The asymmetric conjugate addition is one of the most powerful bond-forming reactions to construct enantioenriched, highly functional carbon skeletons for the total synthesis of natural and biologically active compounds. For reviews see: (a) B. E. Rossiter, N. M. Swingle, *Chem. Rev.* 1992, 771-806; (b) J. Leonard, E. Diez-Barra, S. Merino, *Eur. J. Org. Chem.* 1998, 2051-2061; (c) K. Tomioka, Y Nagaoka, *Comprehensive Asymmetric Catalysis* (Eds.: E. N. Jacobsen, A Pfaltz, H. Yamamoto), Springer, Berlin, 1999, vol. 3, p. 1105-1120; (d) M. Yamaguci, *Comprehensive Asymmetric Catalysis* (Eds.: E. N. Jacobsen, A Pfaltz, H. Yamamoto), Springer, Berlin, 1999, vol. 3, p. 1121-1139; (e) M. P. Sibi, S. Manyem, *Tetrahedron* 2000, 56, 8033-8061; (f) N. Krause, A. Hoffmann-Roder *Synthesis* 2001, 171-196. For general reviews on conjugate additions see: (g) P Perlmutter, *Conjugate Addition Reactions in Organic Synthesis* (Eds.: J. E. Baldwin, P D. Magnus), Pergamon Press, Oxford, 1992; (h) M. E. Jung, *Comprehensive Organic Synthesis* (Ed.: B. M. Trost), Pergamon Press, Oxford, 1991, vol. 4, pp. 1-67. Its strategic importance is evident by considering that a Michael addition can represent the initiating step of more complex inter- and intramolecular tandem processes. For reviews see: (a) L. F Tietze, *Chem. Rev.* 1996, 96, 115-136; (b) R. A. Brunce, *Tetrahedron* 1995, 48, 13103-13159; (c) L. Tietze, U. Beifuss, *Angew. Chem.* 1993, 105, 137-170; *Angew Chem. Int. Ed Engl.* 1993, 32, 131-163; (d) G. H. Posner, *Chem. Rev.* 1986, 86, 831-844.

Among the Michael acceptors, nitroalkenes are very attractive, because the nitro group is the most electron-withdrawing group known. N. Ono, *The Nitro Group in Organic Synthesis*, Wiley-VCH, New York, 2001; D. Seebach, E. W. Colvin, F Lehr, T Weller, *Chimia* 1979, 33, 1-18. Often described as a "synthetic chameleon," the nitro group can serve as masked functionality to be further transformed after the addition has taken place. G. Calderari, D. Seebach, *Helv. Chim. Acta* 1995, 68, 1592-1604. The Nef reaction, the nucleophilic displacement, the reduction to amino group, the Myer reaction, and the conversion into a nitrile oxide are only examples of the transformations that nitro groups can undergo. H. W. Pinnick, *Org. React.* 1990, 38, 655-792; J. U. Nef, *Justus Liebigs Ann. Chem.* 1894, 280, 263-291; R. Tamura, A. Kamimura, N. Ono, *Synthesis* 1991, 423-434; R. C. Larock, *Comprehensive Organic Transformations*, VCH, New York, 1989, pp. 411-415; A. K. Beck, D. Seebach, *Chem. Ber.* 1991, 124, 2897-2911; R. E. Maeri, J. Heinzer, D. Seebach, *Liebigs Ann.* 1995, 1193-1215; M. A. Poupart, G. Fazal, S. Goulet, L. T Mar, *J. Org. Chem.* 1999, 64, 1356-1361; A. G. M. Barrett, C. D. Spilling, *Tetrahedron Lett.* 1988, 29, 5733-5734; D. H. Loyd, D. E. Nichols, *J. Org. Chem.* 1986, 51, 4294-4298; V. Meyer, C. Wurster, *Ber. Dtsch. Chem. Ges.* 1873, 6, 1168-1172; M. J. Kamlet, L. A. Kaplan, J. C. Dacons, *J Org. Chem.* 1961, 26, 4371-4375; T. Mukayama, T Hoshino, *J. Am. Chem. Soc.* 1960, 82, 5339-5342. A number of catalytic synthetic methods have been developed in recent years, making use of nitroalkenes even more attractive. A. G. M. Barret, G. G. Graboski, *Chem. Rev.* 1986, 86, 751-762; R. Ballini, R. Castagnani, M. Petrini, *J. Org. Chem.* 1992, 57, 2160-2162; G. Rosini, R. Ballini, M. Petrini, P Sorrenti, *Synthesis* 1985, 515-517.

Conjugate additions of carbon nucleophiles to alkenyl sulfones in parallel to those to nitroalkenes constitute a class of synthetically valuable C—C bond forming reactions. Accordingly, considerable efforts have been devoted to the development of asymmetric conjugate additions to alkenyl sulfones. Although significant advancements have been made in the use of chiral auxiliary strategy, the realization of a highly enantioselective catalytic conjugate additions with alkenyl sulfones remains elusive. For reviews of enantioselective conjugate additions, see (a) Sibi, M. P.; Manyem, S. *Tetrahedron* 2000, 56, 8033-8061; (b) Krause, N.; Hoffmann-Roder, A. *Synthesis* 2001, 171-196; (c) M. Yamaguchi in Comprehensive Asymmetric Catalysis (Eds.: E. N. Jacobsen, A. Pfaltz, H. Yamamoto), Springer, Heidelberg, 2003, Suppl. 1, Supplement to chap. 31.2, p. 151. (a) Pinheiro, S.; Guingant, A.; Desmaëile, D.; d'Angelo, J. *Tetrahedron: Asymmetry* 1992, 3, 1003; (b) d'Angelo, J.; Revial, G. *Tetrahedron: Asymmetry* 1991, 2, 199. Lin, Y.; Ali, B. E.; Alper, H. *J. Am. Chem. Soc.* 2001, 123, 7719. For a conjugate addition of chiral 1-aminopyrrolidine to alkenyl sulfones see: Enders, D.; Müller, S. F.; Raabe, G.; Runsink, J. *Eur. J. Org. Chem.* 2000, 879. (a) Reddick, J. J.; Cheng, J.; Roush, W. R. *Org. Lett.* 2003, 5, 1967; (b) Sanki, A. K.; Suresh, C. G.; Falgune, U. D.; Pathak, T. *Org. Lett.* 2003, 5, 1285; (c) Ravindran, B.; Sakthivel, K.; Suresh, C. G.; Pathak, T. *J. Org. Chem.* 2000, 65, 2637; (d) Farthing, C.; Marsden, S. P. *Tetrahedron Lett.* 2000, 41, 4235-4238; (e) Hirama, M.; Hioki, H.; Itô, S.; Kabuto, C. *Tetrahedron Lett.* 1988, 29, 3121. For intramolecular Michael addition to alkenyl sulfones see: Carretero, J. C.; Arráyas, R. G. *J. Org. Chem.* 1998, 63, 2993; for a Rh-catalyzed enantioselective conjugate addition of organoboronic acids to trans-β-substituted vinyl sulfones see: Mauleón, P.; Carretero, J. C. *Org. Lett.* 2004, 6, 3195.

Additionally, the conjugate addition of carbon nucleophiles to alkenyl ketones provides a powerful strategy for the creation of all-carbon quaternary stereocenters, due to the accessibility of a wide range of both the Michael donors and acceptors and the proven wide utility of the 1,4-adducts. Remarkably, in spite of numerous great strides made since then in catalytic asymmetric synthesis, this task remains a daunting challenge of undiminished synthetic significance. Wynberg, H.; Helder, R. *Tetrahedron Letters* 1975, 46, 4057-4060. Sawamura, M.; Hamashima, H.; Ito, Y. *J. Am. Chem. Soc.* 1992, 114, 8295-8296. Sasai, H.; Emori, E.; Arai, T.; Shibasaki, M. *Tetrahedron Letters* 1996, 37, 5561-5564. Hamashima, Y.; Hotta, D.; Sodeoka, M. *J. Am. Chem. Soc.* 2002, 124, 11240-11241. Bella, M.; Jørgensen, A. *J. Am. Chem. Soc.* 2004, 126, 5672-5673. For chiral (salen)A1 complex-catalyzed conjugate addition of α-phenyl α-cyanoacetate to an acyclic α,β-unsaturated ketones, see Taylor, M. S.; Zalatan, D. N.; Lerchner, A. M.; Jacobsen, E. N. *J. Am. Chem. Soc.* 2005, 127, 1313-1317. For a special issue focusing on asymmetric catalysis, see: *Proc. Natl. Acad. Sci. USA* 2004, 101, 5347-5850. (b) For a thematic issue for Enantioselective Catalysis see: (Eds: Bolm, C.; Gladysz, J.) *Chem. Rev.* 2003, 103, 2761-3400. (c) *Comprehensive Asymmetric Catalysis,* E. N. Jacobsen, A. Pfaltz, H. Yamamoto Eds, Springer-Verlag, Berlin, 1999, Vol. 1-3. An enantioselective catalytic conjugate addition of α-substituted ketoesters to vinyl ketones was reported by Shibasaki and coworkers in 1994. Sasai, H.; Emori, E.; Arai, T.; Shibasaki, M. *Tetrahedron Letters* 1996, 37, 5561-5564. With a bifunctional chiral La—Na-BINOL complex, the addition of cyclic and acyclic α-substituted ketoesters to methyl vinyl ketone (MVK) proceeded in 62-91% ee. More recently, Sodeoka and coworkers reported a Pd-BINAP complex that afforded 86-93% ee for the conjugate addition of α-substituted ketoesters to methyl and ethyl vinyl ketones. Hamashima, Y.; Hotta, D.; Sodeoka, M. *J. Am. Chem. Soc.* 2002, 124, 11240-11241. These chiral metal complex-mediated reactions, while demonstrating substantial scopes with respect to ketoester donors, afforded greater than 90% ee only with MVK as the Michael acceptor. Moreover, performed at −50 to −20° C., a catalyst loading of 5-10 mol % is required for the reaction to reach completion in 15 to 72 hours. Although representing remarkable progresses, these results underscore both the urgency and challenge for the development of an operationally simple, efficient and rapid enantioselective catalytic conjugate addition of broad substrate scopes for alkenyl ketones.

The present invention relates to the catalytic asymmetric synthesis of chiral compounds from prochiral substrates, such as nitroalkenes, alkenyl sulfones and alkenyl ketones.

Catalytic asymmetric synthesis is providing chemists with new and powerful tools for the efficient synthesis of complex molecules. While many of the catalytic systems are metal-based and rely on chiral Lewis acid and organometallic redox-based catalysis, increasing numbers of asymmetric reactions are catalyzed by chiral nucleophiles, building on the vast assortment of situations in nature in which nucleophiles play pivotal roles. For leading references, see: (a) In *Comprehensive Asymmetric Catalysis;* Jacobsen, E. N., Pfaltz, A., Yamamoto, H., Eds.; Springer: Heidelberg, 1999; (b) In *Asymmetric Catalysis in Organic Synthesis,* Noyori, R., Ed.; Wiley: New York, 1994; (c) In *Asymmetric Synthesis,* 2nd ed.; Ojima, I., Ed.; VCH: New York, 2000; (d) Acc. Chem. Res. 2000, 33, 323. (e) Groger, H.; Wilken, J. *Angew. Chem., Int. Ed.* 2001, 40, 529; (f) Pierre, J.-L. *Chem. Soc. Rev.* 2000, 29, 251-257. (g) Roberts, B. P. *Chem Soc. Rev.* 1999, 28, 25. Chiral amines play a central role in this expanding area of asymmetric catalysis. Although chiral amines have been utilized extensively as chiral ligands, they have also shown great promise in catalyzing a broad range of asymmetric transformations, yielding optically enriched products in high selectivity and yield that may not be accessible through alternative asymmetric technology. Seyden-Penne, J. *Chiral Auxiliaries and Ligands in Asymmetric Synthesis;* Wiley & Sons: New York, 1995.

Historically, the cinchona alkaloids were the first chiral amines to be used in asymmetric catalysis, most notably in the pioneering work of Pracejus from the 1960's on disubstituted ketene alcoholysis. Cinchona alkaloids also possess a rich and colorful history that is rooted in natural products and pharmaceutical chemistry. Turner, R. B.; Woodward, R. B. In *In the Alkaloids;* Manske, R. H. F.; Holmes, H. L., Eds.; Academic Press: New York, 1953; Vol. 3, p 24; Verpoorte, R.; Schripsema, J.; Van der Leer, T. In *In the Alkaloids. Chemistry and Pharmacology,* Brossi, A., Ed.; Academic Press: New York, 1988; Vol. 34; Michael, J. P. In *The Quinoline Alkaloids,* In *Rodd's Chemistry of Carbon Compounds,* 2nd ed.; Sainsbury, M., Ed.; Elsevier: Amsterdam, 1998; 2nd suppl., part F and G, vol 4; 432. They are isolated en masse by extracting the bark of the cinchona tree, which is native to tropical regions. Outside of organic chemistry, the cinchona alkaloids have found wide use as food flavorings (for example as the bitter principle of tonic water) and in the treatment of malaria. Fletcher, D. C. *J. Am. Med. Assoc.* 1976, 236, 305; Mturi, N.; Musumba, C. O.; Wamula, B. M.; Ogutu, B. R.; Newton, C. R. J. C. *CNS Drugs* 2003, 17, 153. Additionally, their roles as ligands, chromatographic selectors, and NMR discriminating agents have been examined extensively over the past thirty years. Several reviews have been published on the catalytic chemistry of cinchona alkaloids over the past four decades. Pracejus, H. Forschr. *Chem. Forsch.* 1967, 8, 493; Morrison, J. D.; Mosher, H. S. *Asymmetric Organic Reactions;* Prentice Hall: Englewood Cliffs, 1971; Wynberg, H. Top. *Stereochem.* 1986, 16, 87; Kacprzak, K.; Gawronski, J. Synthesis 2001, 7, 961.

These reactions appear to be broadly applicable to both research and industrial scale asymmetric synthesis of a wide variety of important chiral building blocks, such as hemiesters, α-amino acids and α-hydroxy acids. Commercially available modified dimeric cinchona alkaloids $(DHQD)_2$ AQN, $(DHQ)_2AQN$ (see FIG. 1), have been identified recently by Deng and coworkers as enantioselective and recyclable catalysts for enantioselective alcoholyses of cyclic anhydrides. However, commercially available $(DHQD)_2$ AQN is expensive. For example, the commercial price (Aldrich Chemical Company) for a mole of $(DHQD)_2AQN$ is more than $100,000.00. Furthermore, the dimeric catalyst is not available in large quantity (e.g., in kilogram quantity). Therefore, stereoselective reactions using dimeric catalysts are not practical on a relatively large scale (>0.1 mol). Consequently, the development of a new generation of monomeric catalysts that is comparably effective to $(DHQD)_2$ AQN, but substantially less costly to produce, is of significant practical value.

Chiral metal and organic catalysts that possess both an acidic and a basic/nucleophilic structural moiety constitute an increasingly powerful platform for the development of asymmetric catalysis. The design and development of such bifunctional chiral catalysts that are efficient yet easily accessible continues to be a major challenge. Wynberg and coworkers demonstrated that natural cinchona alkaloids, via their C9-OH and amine groups, served as bifunctional chiral organic catalysts by activating the nucleophile and electrophile, respectively, for enantioselective reactions. Wynberg, H., Hiemstra, H., *J. Am. Chem. Soc.*, 1981, 103, 417. However, the enantioselectivity of various reactions catalyzed by natural cinchona alkaloids as chiral organic catalysts was usually modest. Hatakeyama and coworkers recently reported a rigid modified cinchona alkaloid that is readily accessible from quinidine. Hatakeyama, S. et al., *J. Am. Chem. Soc.*, 1999, 121, 10219; Hatakeyama, S., *Organic Lett.*, 2003, 5, 3103. The catalyst was found to be efficient for an enantioselective Morita-Baylis-Hillman (MBH) reaction. Both the C6'-OH and the amine groups are believed to be involved in the stabilization of the transition state of the enantioselective MBH reaction.

Remarkably, readily accessible bifunctional organic catalysts that can be derived from either quinidine or quinine have been developed, and their successful use in asymmetric carbon-carbon-bond-forming reactions has been demonstrated.

SUMMARY OF THE INVENTION

One aspect of the present invention relates to quinine-based and quinidine-based catalysts. In certain embodiments, the quinine-based and quinidine-based catalysts contain a hydroxy group at the 6' position. In certain embodiments, the quinine-based and quinidine-based catalysts contain an O-aryl group or an O-aroyl group at the C9 position. In certain embodiments, the quinine-based and quinidine-based catalysts contain an optionally substituted O-diazene group or an optionally substituted O-benzoyl group at the C9 position. In certain embodiments, the quinine-based and quinidine-based catalysts contain a thiourea at the C9 position. In certain embodiments, the quinine-based and quinidine-based catalysts contain an NH(=S)NH-aryl group at the C9 position.

Another aspect of the present invention relates to a method of preparing a chiral, non-racemic compound from a prochiral electron-deficient alkene or prochiral imine, comprising the step of: reacting a prochiral alkene or imine with a nucleophile in the presence of a catalyst; thereby producing a chiral, non-racemic compound; wherein said catalyst is a derivatized quinine or quinidine. In certain embodiments, the nucleophile is a malonate or β-ketoester. In certain embodiments the nucleophile is an alkyl or aryl or aralkyl 2-cyano-2-alkylacetate. In certain embodiments the nucleophile is an alkyl or aryl or aralkyl 2-cyano-2-arylacetate.

Another aspect of the present invention relates to a method of kinetic resolution, comprising the step of: reacting a racemic aldehyde or racemic ketone with a nucleophile in the presence of a derivatized quinine or quinidine, thereby producing a non-racemic, chiral compound. In certain embodiments, the kinetic resolution is dynamic.

BRIEF DESCRIPTION OF THE DRAWINGS

FIG. 4 depicts selected catalysts of the invention.

FIG. 7 depicts asymmetric 1,4-addition-protonation reactions of acyclic Michael donors. Unless noted, all the reactions were run with 0.1 mmol of 2, 0.8 mmol of 1 in 1 mL of toluene with the 20 mol % catalysts at room temperature for the period of time listed in the table. Key: [b]Isolated yield. [c]Determined by $^1$H NMR analysis of crude reaction mixture. [d]Determined by Chiral HPLC or GC analysis (see Supporting Information). [e]Conversion instead of yield was listed. [f]0.5 mL of toluene was used. [g]Pure diastereomer was obtained. [h]Absolute configuration was confirmed after later synthetic study.

FIG. 8 depicts the effect of temperature on the 1,4-addition-protonation reactions of the invention, using catalyst Q-bisCF$_3$TU.

FIG. 10 depicts asymmetric conjugate addition-protonation of alpha-cyano carbonyl compounds with 2-chloroacrylonitrile. Unless noted, reactions were carried out with 0.3 mmol of dotor, 0.9 mmol of acceptor in 3 mL of toluene with 10 mol % catalyst at room temperature. Key: [b]Isolated yield. [c]Determined by $^1$H NMR analysis of crude reaction mixture. [d]Determined by chiral HPLC or GC analysis. [e]Absolute configuration was determined by comparison with previous reported results. [f]The result in parentheses was obtained with QD-catalyst to give opposite enantiomer. [g]The reaction was run at −20° C.

FIG. 11 depicts selected C6' or C9 thiourea chincona alkaloid derivatives which may be used as catalysts in the inventive methods.

FIG. 13 depicts Cinchona Alkaloid-Catalyzed Addition of Dimethyl Malonate (5a) to N-Boc-imine (4D). Catalysts are those shown in FIG. 11. Unless noted, reactions were run with 0.05 mmol of 4D, 0.15 mmol of 5a in 0.10 mL of solvent with 10 mol % catalyst for 16 h. Key: [b]Cinchona alkaloids bearing no thiourea functionality afforded moderate ee. [c]Determined by $^1$H NMR analysis. [d]Determined by HPLC analysis. [e]Reaction was run with Q-1d (20 mol %) at −60° C. for 24 h.

FIG. 14 depicts Enantioselective Mannich Reaction of Malonate 5 to N-Boc-imine 4 Catalyzed by QD-1d and Q-1d (in parentheses). Catalysts are those shown in FIG. 11. Unless noted, reactions were run with 4 (0.20 mmol) and 5 (0.30 mmol) in acetone (0.4 mL) at −60° C. for 36 h, and the results in parentheses were obtained with Q-1d. Key: [b]Isolated yield. [c]Determined by HPLC analysis. [d]Absolute configuration of (+)-6Ab prepared with a QD-1d-catalyzed reaction with determined to be S, see Supporting Information. [e]Reaction was run was 5 mol % QD-1d at −60° C. for 60 h. [f]Reaction was run with 4 (0.30 mmol) and 5 (0.20 mmol) in dichloromethane with high loading of 1d (100 mol %) at 0° C. for 16-24 h with >95% recovery of QD-1d.

DETAILED DESCRIPTION OF THE INVENTION

Figure 1:
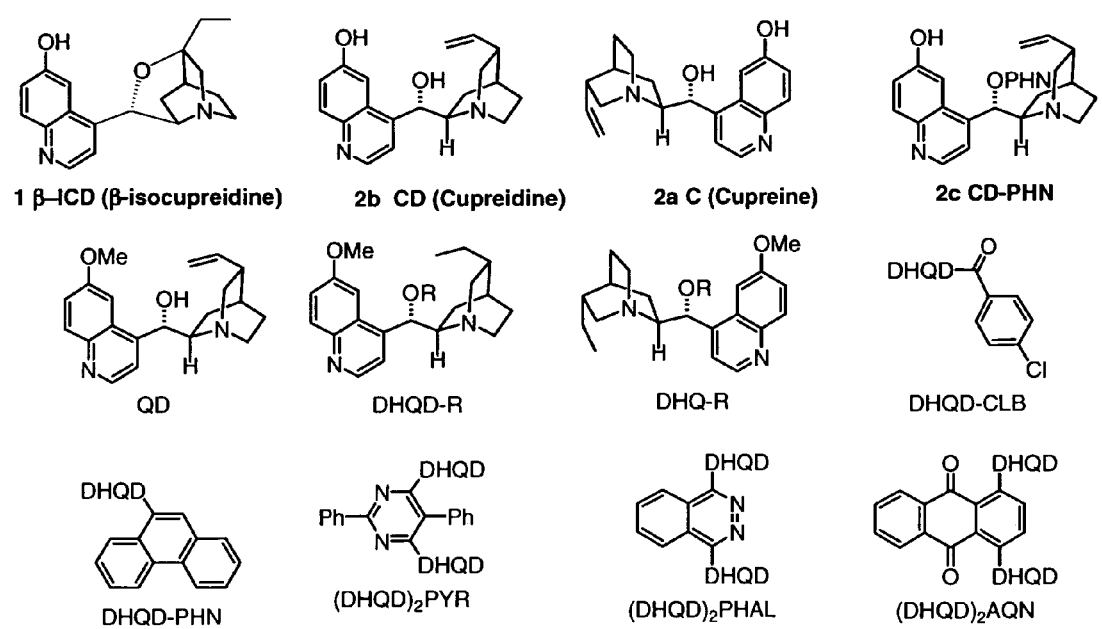
FIG. 1 depicts the structure and nomenclature of several cinchona-alkaloid-based catalysts of the present invention.
Figure 2:
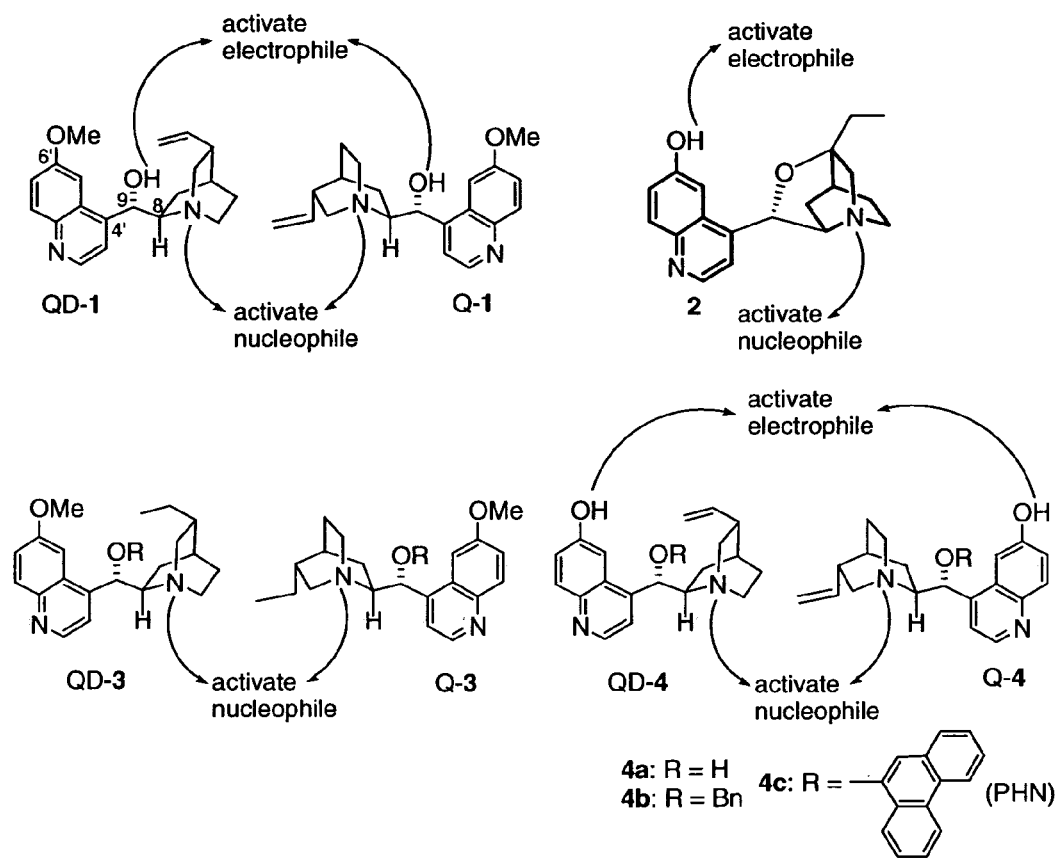
FIG. 2 depicts the bifunctional nature of several cinchona-alkaloid-based catalysts of the present invention.

Enantioselective construction of non-adjacent stereocenters in an acyclic molecule is typically accomplished via a multistep process during which the two stereocenters are generated in different steps. A fundamentally more efficient strategy is to create both stereocenters in one step from readily available achiral starting materials by an asymmetric tandem reaction with an external chiral reagent. While notable examples have been reported in the development of such asymmetric tandem reactions employing a stoichiometric amount of chiral reagents, the implementation of this powerful strategy with efficient catalytic control still represents a formidable challenge.

For selected examples for the construction of non-adjacent hydroxy-amino groups, see: (a)Yamagiwa, N.; Matesunaga, S. *J. Am. Chem. Soc.* 2003, 125, 16178-16179. (b) Minter, A. R.; Fuller, A. A.; Mapp, A. K. *J. Am. Chem. Soc.* 2003, 125, 6846-6847. (c) Josephsohn, N. S.; Snapper, M. L.; Hoveyda, A. H. *J. Am. Chem. Soc.* 2003, 125,4018-4019. (d) Kochi, T.; Tang, T. P.; Ellman, J. A. *J. Am. Chem. Soc.* 2002, 124, 6518-6519. (e) Kobayashi, S.; Hamada, T.; Manabe, K. *J. Am. Chem. Soc.* 2002, 124, 5640-5641. For the construction of non-adjacent diamino groups, see: (f) Matsubara, R.; Nakamura, Y.; Kobayashi, S. *Angew. Chem. Int. Ed.* 2004, 43, 3258-3260. For the construction of nonadjacent diols, see: (g) Flamme, E. M.; Roush, W. R. *J. Am. Chem. Soc.* 2002, 124, 13644-13645. (h) Evans, D. A.; Gauchet-Prunet, J. A. *J. Org. Chem.* 1993, 58, 2446-2453. For the construction of 1,3-related dialkyl groups, see: (i) Tan, Z.; Negishi, E. *Angew. Chem. Int. Ed.* 2004, 43, 2911-2914. (j) Myers, A. G.; Yang, B. H.; Chen, H.; Mckinstry, L.; Kopecky, D. J.; Gleason, J. L. *J. Am. Chem. Soc.* 1997, 119, 6496-6511.

Michael Additions

In particular, the presence of 1,3-tertiary-quaternary stereocenters in many natural products and the lack of efficient method for the constructions of such structural motifs has led to the development of catalytic asymmetric conjugate additions of readily available trisubstituted carbon donors to α-substituted Michael acceptors, for the direct enantioselective creation of 1,3-tertiary-quaternary stereocenters. Wang, X.; Meng, Q.; Perl, N. R.; Xu, Y.; Leighton, J. L. *J. Am. Chem. Soc.* 2005, 127, 12806-12807; Shirakawa, S.; Lombardi, P. L.; Leighton, J. L. *J. Am. Chem. Soc.* 2005, 127, 9974-9975; and Keller, L.; Camara, C.; Pinheiro, A.; Dumas, F.; d'Angelo, J. *Tetrahedron Lett.* 2001, 42, 381-383. To attain synthetically useful enantioselectivity and diastereoselectivity in such a strategy the chiral catalyst is required to exercise efficient stereocontrol in not only the C—C bond forming nucleophilic addition, but also in the subsequent protonation step. Remarkably, herein is disclosed the first realization of such a tandem catalytic conjugate addition-protonation. In addition, the inventive method has been exploited in a concise and flexible asymmetric synthesis of the bromopyrrole alkaloid, manzacidin A. For the asymmetric synthesis of Manzacidin, see: (a) Wehn, P. M.; Du Bois, J. *J. Am. Chem. Soc.* 2002, 124, 12950-12951. (b) Namba, K.; Shinada, T.; Teramoto, T.; Ohfune, Y. *J. Am. Chem. Soc.* 2000, 122, 10708-10709. (c) Lanter, J. C.; Chen, H.; Zhang, X.; Sui, Z. *Org. Lett.* 2005, ASAP. For the asymmetric synthesis of (−)-Dysiherbaine, see: (d) Masaki, H.; Maeyama, J.; Kamada, K.; Esumi, T.; Iwabuchi, Y.; Hatakeyama, S. *J. Am. Chem. Soc.* 2000, 122, 5216-5217. (e) Snider, B. B.; Hawryluk, N. A. *Org. Lett.* 2000, 2, 635-638. For the asymmetric synthesis of (−)-Nakadomarin A, see: Ono, K.; Nakagawa, M.; Nishida, A. *Angew. Chem. Int. Ed.* 2004, 43, 2020-2023.

Figure 3:
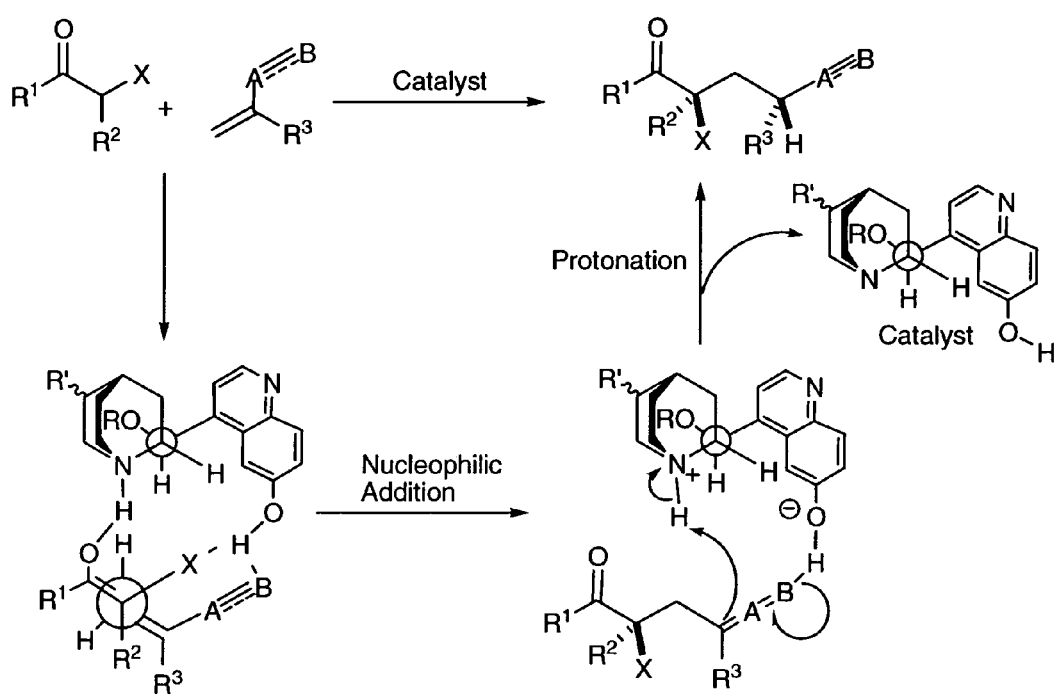
FIG. 3 depicts a proposed mechanism for the enantioselective C—C bond forming nucleophilic addition of a trisubstituted carbon donor to an alpha-substituted Michael acceptor and the subsequent diastereoselective protonation of the resulting enolate.
Figure 9:
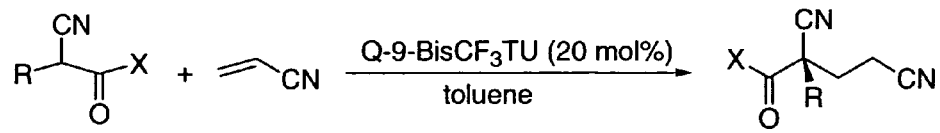
FIG. 9 depicts asymmeteric Michael additions of alpha-cyano carbonyl compounds to arcylonitrile. Unless noted, reactions were carried out with 0.2 mmol of donor, 0.6 mmol of acceptor in 2.0 mL of toluene with Q-catalyst. The results in parentheses were obtained with QD-catalyst to give opposite enantiomer. Key: [b]Isolated yield. [c]Determined by chiral HPLC analysis. [d]Absolute configuration was determined by comparasion with previous results.

The readily accessible modified cinchona alkaloids, such as 1, are highly efficient catalysts for conjugate additions of various trisubstituted carbon nucleophiles to nitroalkenes, α,β-unsaturated sulfones and ketones (see FIG. 1 and FIG. 9). Considering the transition state model indicated from mechanistic studies of the 1-catalyzed conjugate addition of trisubstituted carbon nucleophiles, it was envisioned that catalysts of type 1 would be able to facilitate both the enantioselective C—C bond forming nucleophilic addition of a trisubstituted carbon donor to an α-substituted Michael acceptor and the subsequent diastereoselective protonation of the resulting enolate as illustrated in FIG. 3. Consequently, the cinchona alkaloids of the invention are herein shown to serve as a dual-function chiral catalyst to control the stereoselective generation of both the tertiary and quaternary stereocenters via a tandem asymmetric reaction. For example, the inventive catalysts can promote asymmetric conjugate additions of trisubstituted carbon donors to α-substituted Michael acceptors, as described below.

A 1-catalyzed efficient and general tandem asymmetric conjugate addition-protonation with trisubstituted carbon donors and a Michael acceptor bearing a α-halide has been invented. The synthetic versatility of the halide functionality in combination with a substantial scope of the trisubstituted carbon donors allows this tandem reaction to provide a highly versatile catalytic approach for the asymmetric creation of 1,3-quaternary-tertiary stereocenters.

Figure 5:
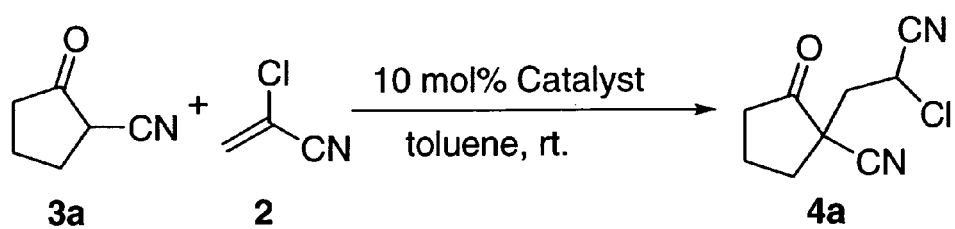
FIG. 5 depicts the results of catalytic Michael additons using the catalysts of the invention. All the reactions, unless noted otherwise, were run with 0.05 mmol of 3a, 0.2 mmol of 2 in toluene with 10 mol % of catalysts. Key: [b]Determined by $^1$H NMR analysis. [c]Determined by Chiral GC [β-CD, 100° C., 4 min then 100° C.-150° C. (0.75° C./min.)]). [d]Reaction was run with 20 mol % of catalyst.

Catalyst screening studies with α-cyanoketone 3a and α-chloro acrylnitrile 2 as model substrates were performed in toluene at room temperature (see FIG. 5). The reaction catalyzed by 1a afforded the best enantioselectivity as well as diastereoselectivity, and at 10 mol % catalyst loading afforded the corresponding 1,4-adduct 4a in 75% ee and 3:1 dr ratio. The ee and dr was improved to 91% and 7:1, respectively, when the reaction was carried out with 20 mol % of 1a and the reaction concentration was decreased from 1.0 M to 0.1 M. In addition to its synthetic significance, the dramatically higher diastereoselectivity afforded by 1a than that by DABCO and other cinchona alkaloids is also of important mechanistic implication because it excludes the possibility that the stereoselective protonation is due to substrate control by the quaternary stereocenter formed in the nucleophilic addition instead of due to catalytic control by 1a.

Figure 6:
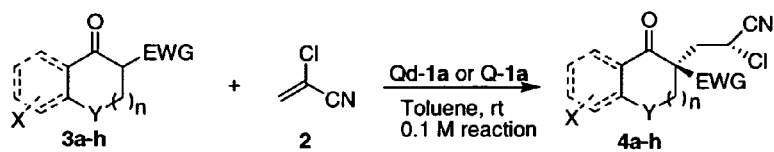
FIG. 6 depicts asymmeteric 1,4-addition-protonation reactions on cyclic Michael donors. Unless noted, all the reactions were run with 0.1 mmol of 3, 0.4 mmol of 2 in 1 mL of toluene with the catalysis of Qd-1a at room temperature for the period of time listed in the table; The results within parentheses are referring to the reaction catalyzed by Q-1a. Key: [b]Isolated yield. [c]Determined by $^1$H NMR analysis of crude reaction mixture. [d]Determined by Chiral HPLC or GC analysis. [e]0.8 mmol of 2 was used instead. [f]Absolute configuration were determined by X-ray analysis.

Following these promising results, the scope of the 1a-catalyzed tandem conjugate addition-protonation with respected to trisubstituted carbon Michael donors was explored (FIGS. 6 and 7). Catalyst 1a was found to be broadly effective for various cyclic trisubstituted carbon donors. The catalyst readily accepted alterations of the cyclic donor in terms of ring size as well as the electronic and the steric property of the substituents attached to the nucleophilic carbon. Thus, reactions of various cyclic α-cyano ketones 3a-3d and ketoesters 3e-3h with 2 proceeded in 71-95% yield to afford the desired adducts 4a-4h containing the 1,3-tertiary-quaternary stereocenters in 7-20:1 dr, and the major diastereomers were produced in 91-99% ee.

The addition of α-phenyl α-cyanoacetate 3i to 2 catalyzed by 1a occurred in 2:1 dr ratio and the major diastereomer was obtained in 79% ee. Structural alterations of the C9-substituent of catalysts 1 could be readily achieved. Importantly, such alterations were shown to have a significant impact on both the enantioselectivity and diastereoselectivity for the asymmetric tandem reaction with 3a and 2. These observations prompted the improvement of the efficiency of catalysts 1 for the tandem asymmetric conjugate addition-protonation with acyclic donors by changing the C9-substituent. Subsequently, it was found that C6'-OH cinchona alkaloids bearing a C9-carboxylate substituent (1d) afforded significantly improved enantioselectivity and diastereoselectivity over those by 1a. Importantly, reactions of a range of acyclic donors with 2 in the presence of 1d occurred in 4-10:1 dr and generated the major diastereomer in 88-93% ee.

Additional examples of aymmeteric conjugate addition of alpha-cyanocarbonyl compounds to acrylonitrile and 2-chloroacrylonitrile, catalyzed by thiourea chincona alkaloid derivatives, are shown in FIGS. 8-10. Additional thoiurea-containing catalysts are shown in FIG. 11.

Encouraged by the unique capacity of this tandem asymmetric reaction in creating stereocomplexity, its high stereoselectivity and considerable substrate scope, new and concise asymmetric total synthesis of biologically and structurally interesting natural products containing 1,3-tertiary-quaternary centers were developed. The bromopyrrole alkaloid, manzacidin A (13), became a particularly attractive target for our total synthesis studies due to its limited supply from natural source. While two concise and highly stereoselective asymmetric syntheses of the closely related manzacidin D were reported by Wehn and Du Bois and Lanter and coworkers, respectively, the only highly stereoselective synthesis of manzacidin A (13) was accomplished by Ohfune and coworkers in 22 steps. In those cases, the N-substituted quaternary and tertiary stereocenters were created in a separate step through either chiral auxiliary-control or substrate control.

Figure 12:
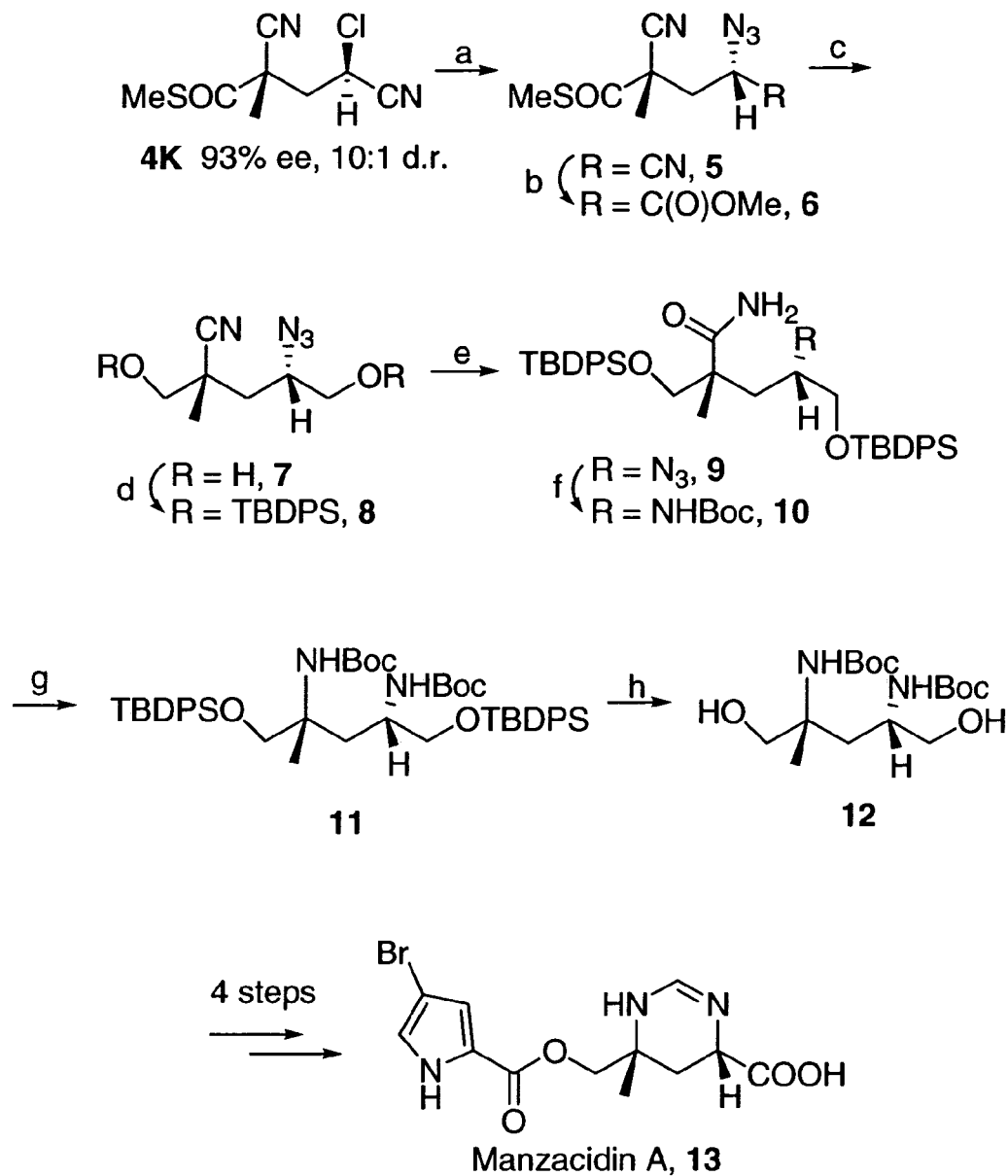
FIG. 12 depicts the catalytic asymmetric formal synthesis of Manzacidin A. Key: a) NaN$_3$, DMSO, rt, 56%, 10:1 d.r. b) TMSCl, MeOH, 0° C., 95%, 9:1 d.r. c) NaBH$_4$, Hg(OAc)$_2$, EtOH, 0 oC, 83%, 9:1 d.r. d) TBDPSCl, imidazole, DMF, rt, 91%, 10:1, d.r. e) [PtH(PMe$_2$OH)(PMe$_2$O)$_2$H], EtOH, H$_2$O, 80oC, 97%, 93% ee, 9:1 d.r. f) Pd/C, Boc$_2$O, EtOH, H$_2$, rt, 68%, 91% ee. g) Pb(OAc)$_4$, tBuOH, reflux, 83%, 11:1 d.r. h) TBAF, THF, rt, 70%, 92% ee, single diasteoremer (TBDPS=tert-butylchlorodiphenylsilane).

It was envisaged that the tetrahydropyrimidine core bearing the 1,3-tertiary-quaternary stereocenters could be constructed via stereospecific transformations of intermediate 4k, which is accessible directly in excellent yield via the highly diastereoselective and enantioselective tandem conjugate addition-protonation catalyzed by 1d (FIG. 12). Substitution of the chloride with azide followed by the selective alcoholysis of the sterically less hindered nitrile group converted 4k to 6 without compromising the stereochemical integrity of the tertiary stereocenter. Both the thioester and ester groups in 6 were then reduced with sodium borohydride. Following protection of the resulting diol, the hydration of the sterically highly hindered nitrile group in 8 was performed by Parkins' procedure to provide amide 9 in excellent yield. An one-pot transformation of the azide in 9 into the corresponding Boc-protected amine furnished amide 10, which readily underwent Hoffman rearrangement under the conditions reported by Burgess to directly form 11 in 83% yield. After the removal of the TBDPS group, diol 12 was isolated in 70% yield as a pure diastereomer in 92% ee. As diol 12 was previously converted to 13 in four steps by Ohfune (Namba, K.; Shinada, T.; Teramoto, T.; Ohfune, Y. *J. Am. Chem. Soc.* 2000, 122, 10708-10709), this 9-step synthesis of 12 constitutes a formal asymmetric total synthesis of Manzacidin A (13) in 13 steps. Importantly, this route will allow the preparation of analogues of 13.

Remarkably, a catalytic tandem asymmetric conjugate addition-protonation reaction with cinchona alkaloids as dual-function chiral catalysts has been discovered. This reaction establishes a new catalytic approach for the one-step construction of 1,3-stereocenters. The synthetic value of this approach in the context of total synthesis of natural products is highlighted in the development of a concise and flexible enantioselective route to Manzacidin A.

Mannich Reactions

Enantioselective Mannich reactions are of fundamental importance to the synthesis of optically active chiral amines. For reviews, see: (a) Có rdova, A. *Acc. Chem. Res.* 2004, 37, 102. (b) Kobayashi, S.; Ueno, M. In *Comprehensive Asymmetric Catalysis Supplement I;* Jacobsen, E. N., Pfaltz, A., Yamamoto, H., Eds.; Springer: Berlin, 2003; Chapter 29.5. (c) Kobayashi, S.; Ishitani, H. *Chem. Rev.* 1999, 99, 1069, and reference therein. Significant progress has been made in the development of efficient chiral metal and organic catalysts for enantioselective Mannich reactions with preactivated enolate nucleophiles such as enolsilane and enolizable carbonyl nucleophiles such as α-keotesters and 1,3-diketones. Kobayashi, S.; Ueno, M.; Saito, S.; Mizuki, Y.; Ishitani, H.; Yamashita, Y. *Proc. Natl. Acad. Sci. U.S.A.* 2004, 101, 5476; Akiyama, T.; Itoh, J.; Yokota, K.; Fuchibe, K. *Angew. Chem., Int. Ed.* 2004, 43, 1566; Josephsohn, N. S.; Snapper, M. L.; Hoveyda, A. H. *J. Am. Chem. Soc.* 2004, 126, 3734; Kobayashi, S.; Matsubara, R.; Nakamura, Y.; Kitagawa, H.; Sugiura, M. *J. Am. Chem. Soc.* 2003, 125, 2507; Wenzel, A. G.; Lalonde, M. P.; Jacobsen, E. N. *Synlett* 2003, 1919; Wenzel, A. G.; Jacobsen, E. N. *J. Am. Chem. Soc.* 2002, 124, 12964; Kobayashi, S.; Hamada, T.; Manabe, K. *J. Am. Chem. Soc.* 2002, 124, 5640; Lou, S.; Taoka, B. M.; Ting, A.; Schaus, S. E. *J. Am. Chem. Soc.* 2005, 127, 11256; Hamashima, Y.; Sasamoto, N.; Hotta, D.; Somei, H.; Umebayashi, N.; Sodeoka, M. *Angew. Chem., Int. Ed.* 2005, 44, 1525; Poulsen, T. B.; Alemparte, C.; Saaby, S.; Bella, M.; Jøorgensen, K. A. *Angew. Chem., Int. Ed.* 2005, 44, 2; and Uraguchi, D.; Terada, M. *J. Am. Chem. Soc.* 2004, 126, 5356. Highly enantioselective, direct Mannich reactions with aldehydes and ketones have also been accomplished with chiral secondary amines and chiral metal complexes. Trost, B. M.; Jaratjaroonphong, J.; Reutrakul, V. *J. Am. Chem. Soc.* 2006, 128, 2778; Mitsumori, S.; Zhang, H.; Cheong, P.; Houk, K. N.; Tanaka, F.; Barbas, C. F., III. *J. Am. Chem. Soc.* 2006, 128, 1040; Kano, T.; Yamaguchi, Y.; Tokuda, O.; Maruoka, K. *J. Am. Chem. Soc.* 2005, 127, 16408; Harada, S.; Handa, S.; Matsunaga, S.; Shibasaki, M. *Angew. Chem., Int. Ed.* 2005, 44, 4365; Okada, A.; Shibuguchi, T.; Ohshima, T.; Masu, H.; Yamaguchi, K.; Shibasaki, M. *Angew. Chem.,Int. Ed.* 2005, 44, 4564; Notz, W.; Watanabe, S.-I.; Chowdari, N. S.; Zhong, G.; Betancort, J. M.; Tanaka, F.; Barbas, C. F., III. *Adv. Synth. Catal.* 2004, 346, 1131; Zhuang, W.; Saaby, S.; Jørgensen, K. A. *Angew. Chem., Int. Ed.* 2004, 43, 4476; Có rdova, A. *Chem. Eur. J.* 2004, 10, 1987; Notz, W.; Tanaka, F.; Barbas, C. F., III. *Acc. Chem. Res.* 2004, 37, 5801; Hayashi, Y.; Tsuboi, W.; Ashimine, I.; Urushima, T.; Shoji, M.; Sakai, K. *Angew. Chem., Int. Ed.* 2003, 42, 3805; List, B.; Pojarliev, P.; Biller, W. T.; Martin, H. J. *J. Am. Chem. Soc.* 2002, 124, 827; and List, B. *J. Am. Chem. Soc.* 2000, 122, 9336. However, a highly enantioselective Mannich reaction of malonates with simple imines remains elusive. Only one Mannich reaction with malonates and an activated N-tosyl-Rimino ester in 39-87% ee has been reported: Marigo, M.; Kjaersgaard, A.; Juhl, K.; Gathergood, N.; Jørgensen, K. A. *Chem. Eur. J.* 2003, 9, 2359. However, if successfully promoted with a practically accessible chiral catalyst under air- and moisture-tolerant conditions, it could provide a highly attractive, convergent approach toward optically active α-amino acids suitably protected for further synthetic elaborations. For reviews on the synthesis of α-amino acids: (a) Ma, J. *Angew. Chem., Int. Ed.* 2003, 42, 4290. (b) Magriotis, P. A. *Angew. Chem., Int. Ed.* 2001, 40, 4377. (c) Liu, M.; Sibi, M. P. *Tetrahedron* 2002, 58, 7991. For recent synthesis of â-amino acids: (a) Berkessel, A.; Cleemann, F.; Mukherjee, S. *Angew. Chem., Int. Ed.* 2005, 44, 2. (b) Hsiao, Y.; Rivera, N. R.; Rosner, T.; Krska, S. W.; Njolito, E.; Wang, F.; Sun, Y.; Armstrong, J. D.; Grabowski, E. J.; Tillyer, R. D.; Spindler, F.; Malan, C. *J. Am. Chem. Soc.* 2004, 126, 9918. (c) Zhou, Y.; Tang, W.; Wang, W.; Li, W.; Zhang, X. *J. Am. Chem. Soc.* 2002, 124, 4952. (d) Sibi, M. P.; Asano, Y. *J. Am. Chem. Soc.* 2001, 123, 9708. (e) Myers, J.; Jacobsen, E. N. *J. Am. Chem. Soc.* 1999, 121, 8959. The realization of such a direct Mannich reaction is particularly challenging as it involves the combination of a weakly reactive imine and a carbonyl nucleophile that is, relative to 1,3-diketones and α-ketoesters, harder to enolize and unsuitable for chiral enamine catalysis.

Herein, the application of cooperative hydrogen-bonding catalysis to develop a cinchona alkaloid-catalyzed, highly enantioselective Mannich reaction with malonates and N-Boc imines is disclosed. Chiral hydrogen-bond donors such as chiral thioureas and phosphoric acid have been identified as effective catalysts for the activation of simple imines toward various enantioselective nucleophilic additions including Mannich reactions with enolsilane and 1,3-diketones. Yoon, T. P.; Jacobsen, E. N. *Angew. Chem., Int. Ed.* 2005, 44, 466; Yoon, T. P.; Jacobsen, E. N. *Science* 2003, 299, 1691; Vachal, P.; Jacobsen, E. N. *J. Am. Chem. Soc.* 2002, 124, 10012; Vachal, P.; Jacobsen, E. N. *Org. Lett.* 2000, 2, 867; Sigman, M. S.; Vachal, P.; Jacobsen, E. N. *Angew. Chem., Int. Ed.* 2000, 39, 1279; Sigman, M. S.; Jacobsen, E. N. *J. Am. Chem. Soc.* 1998, 120, 4901; Xu, X.; Furukawa, T.; Okino, T.; Miyabe, H.; Takemoto, Y. *Chem. Eur. J.* 2006, 12, 466; Okino, T.; Nakamura, S.; Furukawa, T.; Takemoto, Y. *Org. Lett.* 2004, 6, 625; Okino, T.; Hoashi, Y.; Takemoto, Y. *J. Am. Chem. Soc.* 2003, 125, 12672; Bernardi, L.; Fini, F.; Herrera, R. P.; Ricci, A.; Sgarzani, V. *Tetrehedron* 2006, 62, 375. However, chiral hydrogen-bond acceptors such as cinchona alkaloids were shown to be effective for the activation of malonates for enantioselective conjugate additions. Li, H.; Wang, Y.; Tang, L.; Deng, L. *J. Am. Chem. Soc.* 2004, 126, 9906. Therefore it was envisioned that a cinchona alkaloid derivatives bearing a thiourea functionality might act as efficient bifunctional catalysts for a Mannich reaction of malonates with simple imines. Note that Catalyst 1d, accessible in two steps from quinine or quinidine, has been reported by Li, B.; Jiang, L.; Liu, M.; Chen, Y.; Ding, L.; Wu, Y. *Synlett* 2005, 4, 603 and Vakulya, B.; Varga, S.; Csá mpai, A.; Soó s, T. *Org Lett.* 2005, 7, 1967. For recent applications see: Mccooey, S. H.; Connon, S. J. *Angew. Chem., Int. Ed.* 2005, 44, 6367; and Ye, J.; Dixon, D. J.; Hynes, P. *Chem. Commun.* 2005, 35, 4481.

Figure 15:
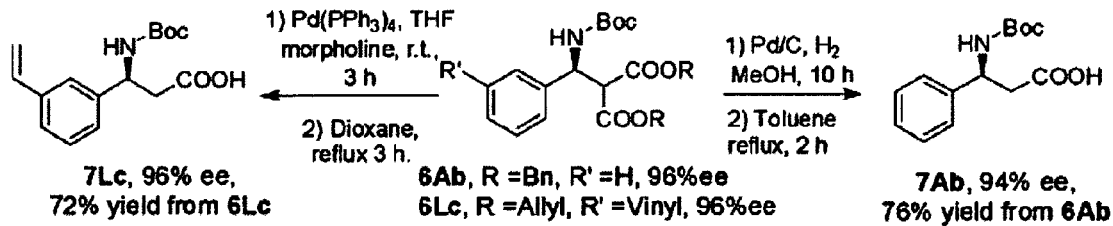
FIG. 15 depicts [A] Enantioselective Mannich Reactions of α-Ketoester 8 to N-Boc-imine 4A Catalyzed by QD-1d and Q-1d (in parentheses); catalysts are those shown in FIG. 11; unless noted, reactions were run with 4A (0.20 mmol) and 8 (0.30 mmol) in acetone (0.4 mL), and the results in parentheses were obtained with Q-1d; Key: [b]Isolated yield, [c]Determined by $^1$H NMR analysis, and [d]Determined by HPLC analysis. It also depicts [B] the synthesis of N-Boc-α-amino acids.

Accordingly, a study of cinchona alkaloid derivatives bearing either a 6'- or 9-thiourea functionality (FIG. 11) as catalysts for the addition of dimethyl malonate 5a to the N-Boc-protected imine 4D in dichloromethane was initiated. As summarized in FIG. 13, 6'- or 9-thiourea cinchona alkaloids bearing an electron-withdrawing aryl substituent emerged as the most effective catalysts. The Mannich reaction with catalysts thiourea Q-1d and thiourea Q-3 took place in 77% and 72% ee, respectively (entries 4 and 7). A study of the reaction with the synthetically more accessible thiourea Q-1d in various solvents identified acetonitrile and acetone as suitable alternatives to dichloromethane (entries 8 and 9). Interestingly, reactions in these solvents responded differently to temperature change. For reactions at −20° C. vs those at room temperature, the enantioselectivity was slightly increased in dichloromethane but decreased noticeably in acetonitrile. A more pronounced positive temperature effect on the enantioselectivity was observed in acetone, which led us to a highly enantioselective, completed reaction of 4D with 5a at −60° C. (entry 13). The scope of the enantioselective Mannich reaction catalyzed by both thiourea Q-1d and thiourea QD-1d was investigated under the optimized condition identified above (FIG. 14). The enantioselectivity of thiourea catalyst QD-1d was found to be nearly independent of the steric properties of the aryl imines. Reactions with o-, m-, and p-tolyl imines (4B-D) in the presence of thiourea QD-1d took place in 97-99% ee. Exceedingly high enantioselectivity could also be obtained for a variety of heteroaryl and aryl imines of varying electronic properties (4E-L), including electron-rich aryl imines. It is noteworthy that very good enantioselectivity could be attained for N-Boc alkyl imines, including even R-unbranched alkyl imines (4M-O). Although high loading of thiourea QD-1d (100 mol %) was required to sustain a useful level of enantioselectivity, thiourea QD-1d could be readily recycled in greater than 95% yield. These results with 4M-N represent the first highly enantioselective Mannich reactions with N-Boc R-unbranched alkyl imines (entries 13-14). Thiourea catalyst 1d also tolerated malonates of different bulk. This allows the conversion of amine 6 to α-amino acid 7 without using strongly acidic or basic conditions (FIG. 15[B]). The thiourea 1d-catalyzed Mannich reaction is also applicable to α-ketoesters (FIG. 15[A]). Importantly, steric variations of the keto substituent are readily accepted by thiourea catalyst 1d, thereby allowing the Mannich reaction to provide access to a wide variety of optically active α-amino ketones.

In conclusion, by exploring cooperative hydrogen-bonding catalysis with a readily accessible bifunctional cinchona alkaloid catalyst, a highly enantioselective direct Mannich reactions of N-Boc aryl and alkyl imines with malonates and α-ketoesters has been developed. (See also Tillman, A. L.; Ye, J.; Dixon, D. *J. Chem. Commun.* 2006, 1191, which reports a Mannich reaction of malonates and α-ketoesters to N-Boc aryl imines). This leads to the establishment of a convergent enantioselective synthesis of N-Boc α-amino acids from readily available starting materials under mild, moisture- and air-compatible compounds.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, anines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents, such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "Bronsted base" is art-recognized and refers to an uncharged or charged atom or molecule, e.g., an oxide, amine, alkoxide, or carbonate, that is a proton acceptor.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an ee for a particular enantiomer that is larger than the ee of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderence of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from about 0.001 to about 50 mole percent, still more preferably from about 0.01 to about 10 mole percent, and even more preferably from about 0.1 to about 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess A (ee)=(% Enantiomer A)−(% Enantiomer B)

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than about 20%, more preferably greater than about 50%, even more preferably greater than about 70%, and most preferably greater than about 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least about 75%. "Substantially non-racemic" refers to preparations of the catalyst which have greater than about 90% ee for a given enantiomer of the catalyst, more preferably greater than about 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that may be represented by the general formulas:

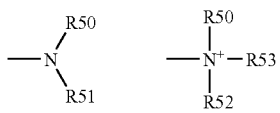

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

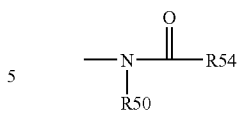

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

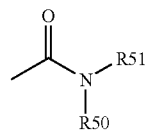

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

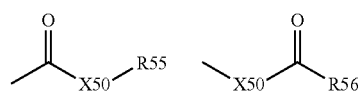

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

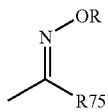

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, -0-alkynyl, —O—(CH$_2$)$_m$—R61, where m and R61 are described above.

The term "sulfonate" is art recognized and refers to a moiety that may be represented by the general formula:

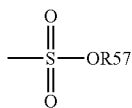

in which R57 is an electron pair, hydrogen, alkyl, cycloalkyl, or aryl.

The term "sulfate" is art recognized and includes a moiety that may be represented by the general formula:

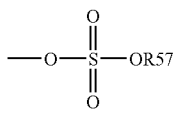

in which R57 is as defined above.

The term "sulfonamido" is art recognized and includes a moiety that may be represented by the general formula:

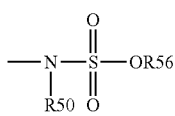

in which R50 and R56 are as defined above.

The term "sulfamoyl" is art-recognized and refers to a moiety that may be represented by the general formula:

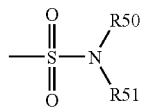

in which R50 and R51 are as defined above.

The term "sulfonyl" is art-recognized and refers to a moiety that may be represented by the general formula:

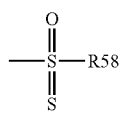

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

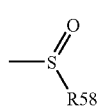

in which R58 is defined above.

The term "phosphoryl" is art-recognized and may in general be represented by the formula:

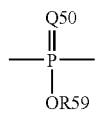

wherein Q50 represents S or O, and R59 represents hydrogen, a lower alkyl or an aryl. When used to substitute, e.g., an alkyl, the phosphoryl group of the phosphorylalkyl may be represented by the general formulas:

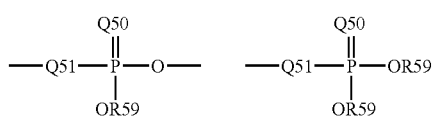

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

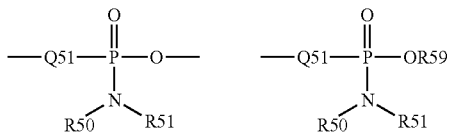

wherein Q51, R50, R51 and R59 are as defined above.

The term "phosphonamidite" is art-recognized and may be represented in the general formulas:

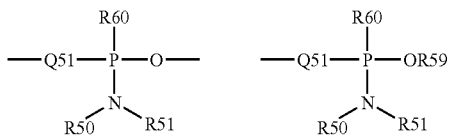

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

The term "perfluoroalkyl" is art-recognized and refers to an alkyl group in which all hydrogens have been replaced with fluorines. For example, trifluoromethyl and pentafluoroethyl are perfluoroalkyl groups.

The term "1-adamantyl" is art-recognized and includes a moiety represented by the formula:

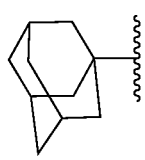

The term "(−)-menthyl" is art-recognized and includes a moiety represented by the formula:

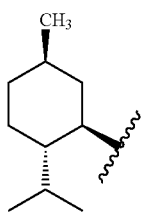

The term "(+)-menthyl" is art-recognized and includes a moiety represented by the formula:

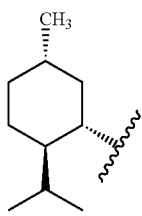

The term "isobornyl" is art-recognized and includes a moiety represented by the formula:

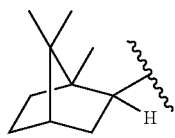

The term "isopinocamphyl" is art-recognized and includes a moiety represented by the formula:

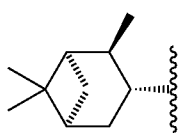

The term "(+)-fenchyl" is art-recognized and includes a moiety represented by the formula:

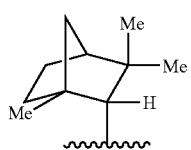

The abbreviation "QD" represents a moiety according to the following formula:

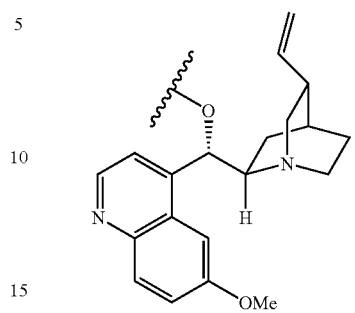

The term "Q" represents a moiety according to the following formula:

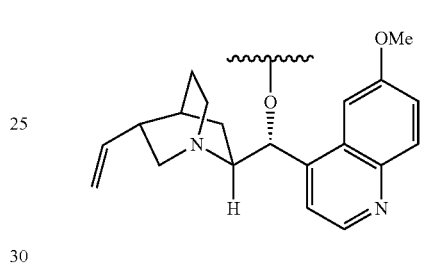

The terms "β-amino β-cyano ketone", "β-amino β-keto ester", "β-amino β-cyano ester" and "β-amino 1,3-diketone" represent a moitey according to one of the following formulas:

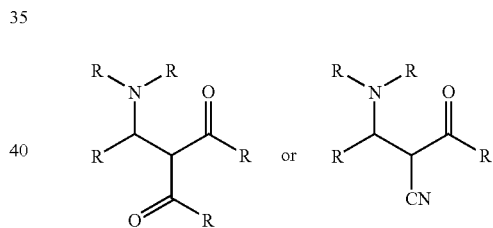

wherein R is independently defined for each occurrence.

Catalysts of the Invention

The catalysts employed in the subject methods are non-racemic chiral amines which present an asymmetric environment, causing stereochemical discrimination between two stereogenic faces of an alkene; or two or more prochiral moieties (e.g., related by symmetry in a prochiral or meso molecule, (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

One aspect of the present invention relates to a compound represented by formula I:

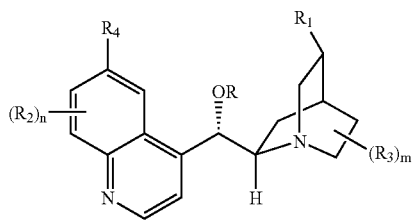

I wherein, independently for each occurrence:

R represents substituted or unsubstituted nitrogen-containing heteroaryl, or benzoyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and

R4 represents —OH.

In certain embodiments, the compounds of the present invention are represented by formula I and any of the attendant definitions, wherein R represents substituted or unsubstituted diazene.

In certain embodiments, the compounds of the present invention are represented by formula I and any of the attendant definitions, wherein R represents 5-chloro-3,6-diphenyl-2,4-diazene.

In certain embodiments, the compounds of the present invention are represented by formula I and any of the attendant definitions, wherein R represents halobenzoyl.

In certain embodiments, the compounds of the present invention are represented by formula I and any of the attendant definitions, wherein R represents 4-chlorobenzoyl.

In certain embodiments, the compounds of the present invention are represented by formula I and any of the attendant definitions, wherein $R_1$ is alkyl.

In certain embodiments, the compounds of the present invention are represented by formula I and any of the attendant definitions, wherein $R_1$ is ethyl.

In certain embodiments, the compounds of the present invention are represented by formula I and any of the attendant definitions, wherein $R_1$ is alkenyl.

In certain embodiments, the compounds of the present invention are represented by formula I and any of the attendant definitions, wherein $R_1$ is —CH=$CH_2$.

In certain embodiments, the compounds of the present invention are represented by formula I and any of the attendant definitions, wherein n is 0.

In certain embodiments, the compounds of the present invention are represented by formula I and any of the attendant definitions, wherein m is 0.

In certain embodiments, the compounds of the present invention are represented by formula I and any of the attendant definitions, wherein R is diazene and $R_1$ is ethyl.

In certain embodiments, the compounds of the present invention are represented by formula I and any of the attendant definitions, wherein R is halobenzoyl and $R_1$ is ethyl.

In certain embodiments, the compounds of the present invention are represented by formula I and any of the attendant definitions, wherein R represents 5-chloro-3,6-diphenyl-2,4-diazene; and $R_1$ is ethyl.

In certain embodiments, the compounds of the present invention are represented by formula I and any of the attendant definitions, wherein R represents 4-chlorobenzoyl; and $R_1$ is ethyl.

In certain embodiments, the compounds of the present invention are represented by formula I and any of the attendant definitions, wherein R is diazene and $R_1$ is —CH=$CH_2$.

In certain embodiments, the compounds of the present invention are represented by formula I and any of the attendant definitions, wherein R is halobenzoyl and $R_1$ is —CH=$CH_2$.

In certain embodiments, the compounds of the present invention are represented by formula I and any of the attendant definitions, wherein R represents 5-chloro-3,6-diphenyl-2,4-diazene; and $R_1$ is —CH=$CH_2$.

In certain embodiments, the compounds of the present invention are represented by formula I and any of the attendant definitions, wherein R represents 4-chlorobenzoyl; and $R_1$ is —CH=$CH_2$.

In certain embodiments, the compounds of the present invention are represented by formula I and any of the attendant definitions, wherein R is diazene; $R_1$ is ethyl; m is 0; and n is 0.

In certain embodiments, the compounds of the present invention are represented by formula I and any of the attendant definitions, wherein R is halobenzoyl; $R_1$ is ethyl; m is 0; and n is 0.

In certain embodiments, the compounds of the present invention are represented by formula I and any of the attendant definitions, wherein R represents 5-chloro-3,6-diphenyl-2,4-diazene; $R_1$ is ethyl; m is 0; and n is 0.

In certain embodiments, the compounds of the present invention are represented by formula I and any of the attendant definitions, wherein R represents 4-chlorobenzoyl; $R_1$ is ethyl; m is 0; and n is 0.

In certain embodiments, the compounds of the present invention are represented by formula I and any of the attendant definitions, wherein R is diazene; $R_1$ is —CH=$CH_2$; m is 0; and n is 0.

In certain embodiments, the compounds of the present invention are represented by formula I and any of the attendant definitions, wherein R is halobenzoyl; $R_1$ is —CH=$CH_2$; m is 0; and n is 0.

In certain embodiments, the compounds of the present invention are represented by formula I and any of the attendant definitions, wherein R represents 5-chloro-3,6-diphenyl-2,4-diazene; $R_1$ is —CH=CH$_2$; m is 0; and n is 0.

In certain embodiments, the compounds of the present invention are represented by formula I and any of the attendant definitions, wherein R represents 4-chlorobenzoyl; $R_1$ is —CH=CH$_2$; m is 0; and n is 0.

Another aspect of the present invention relates to a compound represented by formula II:

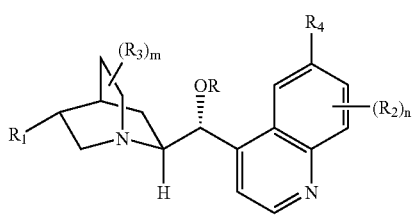

wherein, independently for each occurrence:

R represents substituted or unsubstituted nitrogen-containing heteroaryl, or benzoyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the compounds of the present invention are represented by formula II and any of the attendant definitions, wherein R represents substituted or unsubstituted diazene.

In certain embodiments, the compounds of the present invention are represented by formula II and any of the attendant definitions, wherein R represents 5-chloro-3,6-diphenyl-2,4-diazene.

In certain embodiments, the compounds of the present invention are represented by formula II and any of the attendant definitions, wherein R represents halobenzoyl.

In certain embodiments, the compounds of the present invention are represented by formula II and any of the attendant definitions, wherein R represents 4-chlorobenzoyl.

In certain embodiments, the compounds of the present invention are represented by formula II and any of the attendant definitions, wherein $R_1$ is alkyl.

In certain embodiments, the compounds of the present invention are represented by formula II and any of the attendant definitions, wherein $R_1$ is ethyl.

In certain embodiments, the compounds of the present invention are represented by formula II and any of the attendant definitions, wherein $R_1$ is alkenyl.

In certain embodiments, the compounds of the present invention are represented by formula II and any of the attendant definitions, wherein $R_1$ is —CH=CH$_2$.

In certain embodiments, the compounds of the present invention are represented by formula II and any of the attendant definitions, wherein n is 0.

In certain embodiments, the compounds of the present invention are represented by formula II and any of the attendant definitions, wherein m is 0.

In certain embodiments, the compounds of the present invention are represented by formula II and any of the attendant definitions, wherein R is diazene and $R_1$ is ethyl.

In certain embodiments, the compounds of the present invention are represented by formula II and any of the attendant definitions, wherein R is halobenzoyl and $R_1$ is ethyl.

In certain embodiments, the compounds of the present invention are represented by formula II and any of the attendant definitions, wherein R represents 5-chloro-3,6-diphenyl-2,4-diazene; and $R_1$ is ethyl.

In certain embodiments, the compounds of the present invention are represented by formula II and any of the attendant definitions, wherein R represents 4-chlorobenzoyl; and $R_1$ is ethyl.

In certain embodiments, the compounds of the present invention are represented by formula II and any of the attendant definitions, wherein R is diazene and $R_1$ is —CH=CH$_2$.

In certain embodiments, the compounds of the present invention are represented by formula II and any of the attendant definitions, wherein R is halobenzoyl and $R_1$ is —CH=CH$_2$.

In certain embodiments, the compounds of the present invention are represented by formula II and any of the attendant definitions, wherein R represents 5-chloro-3,6-diphenyl-2,4-diazene; and $R_1$ is —CH=CH$_2$.

In certain embodiments, the compounds of the present invention are represented by formula II and any of the attendant definitions, wherein R represents 4-chlorobenzoyl; and $R_1$ is —CH=CH$_2$.

In certain embodiments, the compounds of the present invention are represented by formula II and any of the attendant definitions, wherein R is diazene; $R_1$ is ethyl; m is 0; and n is 0.

In certain embodiments, the compounds of the present invention are represented by formula II and any of the attendant definitions, wherein R is halobenzoyl; $R_1$ is ethyl; m is 0; and n is 0.

In certain embodiments, the compounds of the present invention are represented by formula II and any of the attendant definitions, wherein R represents 5-chloro-3,6-diphenyl-2,4-diazene; $R_1$ is ethyl; m is 0; and n is 0.

In certain embodiments, the compounds of the present invention are represented by formula II and any of the attendant definitions, wherein R represents 4-chlorobenzoyl; $R_1$ is ethyl; m is 0; and n is 0.

In certain embodiments, the compounds of the present invention are represented by formula II and any of the attendant definitions, wherein R is diazene; $R_1$ is —CH=CH$_2$; m is 0; and n is 0.

In certain embodiments, the compounds of the present invention are represented by formula II and any of the attendant definitions, wherein R is halobenzoyl; $R_1$ is —CH=CH$_2$; m is 0; and n is 0.

In certain embodiments, the compounds of the present invention are represented by formula II and any of the attendant definitions, wherein R represents 5-chloro-3,6-diphenyl-2,4-diazene; $R_1$ is —CH=CH$_2$; m is 0; and n is 0.

In certain embodiments, the compounds of the present invention are represented by formula II and any of the attendant definitions, wherein R represents 4-chlorobenzoyl; $R_1$ is —CH=CH$_2$; m is 0; and n is 0.

Another aspect of the present invention relates to a compound represented by formula III:

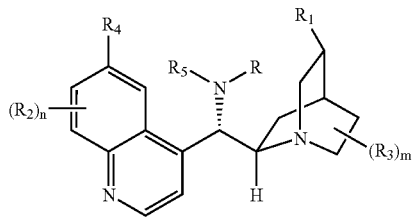

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the compounds of the present invention are represented by formula III and any of the attendant definitions, wherein R is —C(=S)N(H)-aryl.

In certain embodiments, the compounds of the present invention are represented by formula III and any of the attendant definitions, wherein R is —C(=S)N(H)-monocyclic aryl.

In certain embodiments, the compounds of the present invention are represented by formula III and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the compounds of the present invention are represented by formula III and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the compounds of the present invention are represented by formula III and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3, 5-bisCF$_3$-Ph).

In certain embodiments, the compounds of the present invention are represented by formula III and any of the attendant definitions, wherein $R_1$ is alkyl.

In certain embodiments, the compounds of the present invention are represented by formula III and any of the attendant definitions, wherein $R_1$ is ethyl.

In certain embodiments, the compounds of the present invention are represented by formula III and any of the attendant definitions, wherein $R_1$ is alkenyl.

In certain embodiments, the compounds of the present invention are represented by formula III and any of the attendant definitions, wherein $R_1$ is —CH=CH$_2$.

In certain embodiments, the compounds of the present invention are represented by formula III and any of the attendant definitions, wherein $R_4$ is hydrogen or ether.

In certain embodiments, the compounds of the present invention are represented by formula III and any of the attendant definitions, wherein $R_4$ is hydrogen or —OCH$_3$.

In certain embodiments, the compounds of the present invention are represented by formula III and any of the attendant definitions, wherein $R_5$ is hydrogen.

In certain embodiments, the compounds of the present invention are represented by formula III and any of the attendant definitions, wherein m is 0.

In certain embodiments, the compounds of the present invention are represented by formula III and any of the attendant definitions, wherein n is 0.

In certain embodiments, the compounds of the present invention are represented by formula III and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the compounds of the present invention are represented by formula III and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the compounds of the present invention are represented by formula III and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the compounds of the present invention are represented by formula III and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the compounds of the present invention are represented by formula III and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the compounds of the present invention are represented by formula III and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

Another aspect of the present invention relates to a compound represented by formula IV:

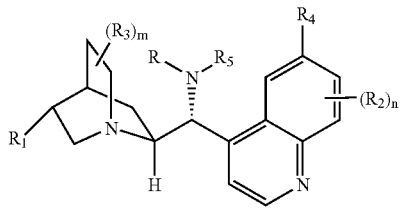

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the compounds of the present invention are represented by formula IV and any of the attendant definitions, wherein R is —C(=S)N(H)-aryl.

In certain embodiments, the compounds of the present invention are represented by formula IV and any of the attendant definitions, wherein R is —C(=S)N(H)-monocyclic aryl.

In certain embodiments, the compounds of the present invention are represented by formula IV and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the compounds of the present invention are represented by formula IV and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the compounds of the present invention are represented by formula IV and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the compounds of the present invention are represented by formula IV and any of the attendant definitions, wherein $R_1$ is alkyl.

In certain embodiments, the compounds of the present invention are represented by formula IV and any of the attendant definitions, wherein $R_1$ is ethyl.

In certain embodiments, the compounds of the present invention are represented by formula IV and any of the attendant definitions, wherein $R_1$ is alkenyl.

In certain embodiments, the compounds of the present invention are represented by formula IV and any of the attendant definitions, wherein $R_1$ is —CH=CH$_2$.

In certain embodiments, the compounds of the present invention are represented by formula IV and any of the attendant definitions, wherein $R_4$ is hydrogen or ether.

In certain embodiments, the compounds of the present invention are represented by formula IV and any of the attendant definitions, wherein $R_4$ is hydrogen or 13 OCH$_3$.

In certain embodiments, the compounds of the present invention are represented by formula IV and any of the attendant definitions, wherein $R_5$ is hydrogen.

In certain embodiments, the compounds of the present invention are represented by formula IV and any of the attendant definitions, wherein m is 0.

In certain embodiments, the compounds of the present invention are represented by formula IV and any of the attendant definitions, wherein n is 0.

In certain embodiments, the compounds of the present invention are represented by formula IV and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the compounds of the present invention are represented by formula IV and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the compounds of the present invention are represented by formula IV and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the compounds of the present invention are represented by formula IV and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the compounds of the present invention are represented by formula IV and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the compounds of the present invention are represented by formula IV and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

Another aspect of the present invention relates to a compound represented by formula V:

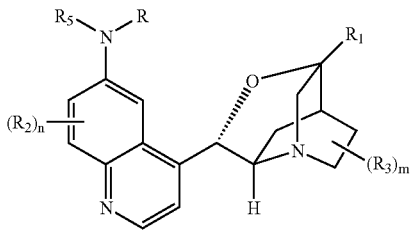

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the compounds of the present invention are represented by formula V and any of the attendant definitions, wherein R is —C(=S)N(H)-aryl.

In certain embodiments, the compounds of the present invention are represented by formula V and any of the attendant definitions, wherein R is —C(=S)N(H)-monocyclic aryl.

In certain embodiments, the compounds of the present invention are represented by formula V and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the compounds of the present invention are represented by formula V and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the compounds of the present invention are represented by formula V and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the compounds of the present invention are represented by formula V and any of the attendant definitions, wherein $R_1$ is alkyl.

In certain embodiments, the compounds of the present invention are represented by formula V and any of the attendant definitions, wherein $R_1$ is ethyl.

In certain embodiments, the compounds of the present invention are represented by formula V and any of the attendant definitions, wherein $R_1$ is alkenyl.

In certain embodiments, the compounds of the present invention are represented by formula V and any of the attendant definitions, wherein $R_1$ is —CH=CH$_2$.

In certain embodiments, the compounds of the present invention are represented by formula V and any of the attendant definitions, wherein $R_5$ is hydrogen.

In certain embodiments, the compounds of the present invention are represented by formula V and any of the attendant definitions, wherein m is 0.

In certain embodiments, the compounds of the present invention are represented by formula V and any of the attendant definitions, wherein n is 0.

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(4-t-Bu-Ph).

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(2-i-Pr-Ph).

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(Ph).

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(3,5-bisCF$_3$-Ph).

In certain embodiments, the compounds of the present invention are represented by formula V and any of the attendant definitions, wherein $R_1$ is —CH$_2$CH$_3$; m is 0; n is 0; $R_5$ is hydrogen; and R is —C(=S)N(H)-(3,5-bisCF$_3$-Ph).

Methods of the Invention—Catalyzed Reactions

In one aspect of the present invention there is provided a process for stereoselectively producing compounds with at least one stereogenic center from prochiral, or racemic starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective addition process which comprises combining a nucleophilic reactant, a prochiral or chiral substrate, and at least a catalytic amount of non-racemic chiral catalyst of particular characteristics (as described below). Suitable substrates for the reaction include prochiral electron-deficient alkenes, prochiral aldehydes and prochiral ketones susceptible to attack by the nucleophile. The combination of substrate, nucleophile, and catalyst is maintained under conditions appropriate for the chiral catalyst to catalyze the addition of the nucleophilic reactant to the prochiral electron-deficient alkene or prochiral aldehyde or prochiral ketone. This reaction can be applied to enantioselective processes as well as diastereoselective processes. It may also be adapted for regioselective reactions. Below are examples of enantioselective and diastereoselective reactions, kinetic resolutions, dynamic kinetic resolutions, and regioselective reactions which may be catalyzed according to the present invention.

Moreover, the methods of the invention can provide optically active products with very high stereoselectivity (e.g., enantioselectivity or diastereoselectivity) or regioselectivity. In preferred embodiments of the subject reactions, products with enantiomeric excess or diastereomeric excess of greater than about 50%, greater than about 70%, greater than about 90%, and greater than about 95% can be obtained. The methods of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. The invention expressly contemplates the preparation of end-products and synthetic intermediates which are useful for the preparation or development or both of therapeutic compounds.

Asymmetric Addition of Enolates to Electron-Deficient Alkenes

One aspect of the present invention relates to a method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula I:

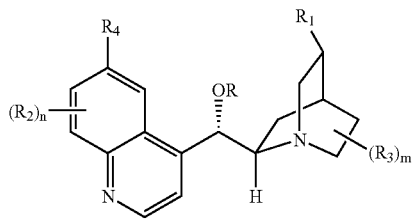

I wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and $R_1$ is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and $R_1$ is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=CH$_2$; m is 0; and n is 0.

In certain embodiments, the present invention relates to the aforementioned method and any of the attendant definitions, wherein R is diazene; $R_1$ is —CH=CH$_2$; m is 0; and n is 0.

In certain embodiments, the present invention relates to the aforementioned method and any of the attendant definitions, wherein R is halobenzoyl; $R_1$ is —CH=CH$_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=CH$_2$; m is 0; and n is 0.

In certain embodiments, the present invention relates to the aforementioned method and any of the attendant definitions, wherein R represents 4-chlorobenzoyl; $R_1$ is —CH=CH$_2$; m is 0; and n is 0.

In certain embodiments, the present invention relates to the aforementioned method and any of the attendant definitions, wherein said electron-deficient alkene is represented by C:

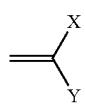

wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

Another aspect of the present invention relates to a method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula II:

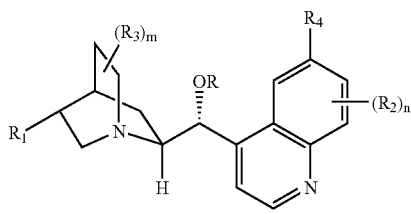

wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and $R_1$ is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and $R_1$ is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=$CH_2$; m is 0; and n is 0.

In certain embodiments, the present invention relates to the aforementioned method and any of the attendant definitions, wherein R is diazene; $R_1$ is —CH=$CH_2$; m is 0; and n is 0.

In certain embodiments, the present invention relates to the aforementioned method and any of the attendant definitions, wherein R is halobenzoyl; $R_1$ is —CH=$CH_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=$CH_2$; m is 0; and n is 0.

In certain embodiments, the present invention relates to the aforementioned method and any of the attendant definitions, wherein R represents 4-chlorobenzoyl; $R_1$ is —CH=$CH_2$; m is 0; and n is 0.

In certain embodiments, the present invention relates to the aforementioned method and any of the attendant definitions, wherein said electron-deficient alkene is represented by C:

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

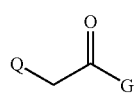

D wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diasteromeric excess greater than about 95%.

Another aspect of the present invention relates to a method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

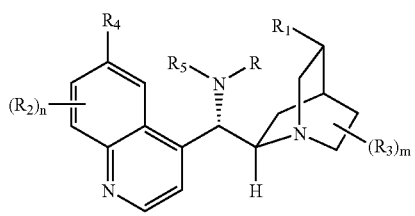

III wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; 4 is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

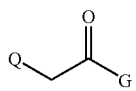

D wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

Another aspect of the present invention relates to a method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

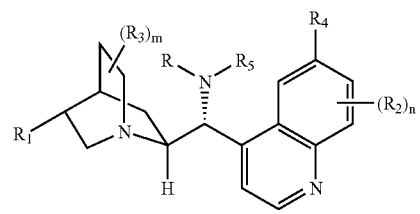

IV wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

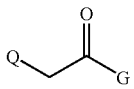

wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

Another aspect of the present invention relates to a method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula V:

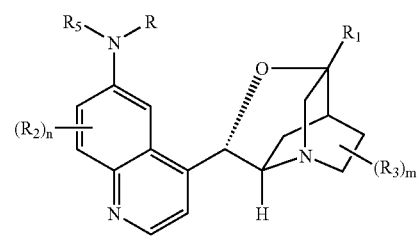

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein R$_1$ is alkyl.

In certain embodiments, the present invention relates to the aforementioned method and any of the attendant definitions, wherein R$_1$ is ethyl.

In certain embodiments, the present invention relates to the aforementioned method and any of the attendant definitions, wherein R$_1$ is alkenyl.

In certain embodiments, the present invention relates to the aforementioned method and any of the attendant definitions, wherein R$_1$ is —CH=CH$_2$.

In certain embodiments, the present invention relates to the aforementioned method and any of the attendant definitions, wherein R$_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(4-t-Bu-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(2-i-Pr-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(3,5-bisCF$_3$-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

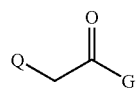

D wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

Asymmetric Addition of Enolates to Imines (Mannich Reactions)

One aspect of the present invention relates to a method of preparing a chiral, non-racemic β-amino β-cyano ketone, chiral, non-racemic β-amino β-keto ester, chiral, non-racemic β-amino β-cyano ester or chiral, non-racemic β-amino 1,3-diketone, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula III:

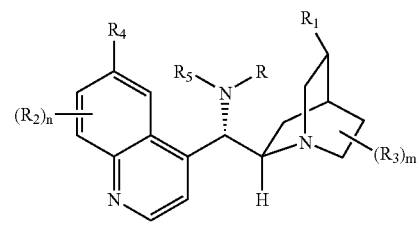

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)-C6(R')$_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

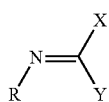

wherein

R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F:

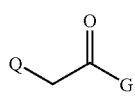

wherein

Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

One aspect of the present invention relates to a method of preparing a chiral, non-racemic β-amino β-cyano ketone, chiral, non-racemic β-amino β-keto ester, chiral, non-racemic β-amino β-cyano ester or chiral, non-racemic β-amino 1,3-diketone, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula IV:

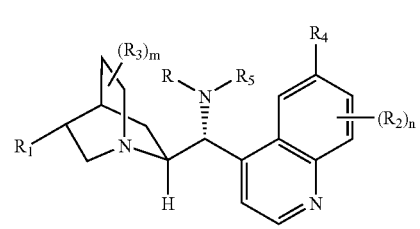

IV wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein R$_1$ is alkyl.

In certain embodiments, the present invention relates to the aforementioned method and any of the attendant definitions, wherein R$_1$ is ethyl.

In certain embodiments, the present invention relates to the aforementioned method and any of the attendant definitions, wherein R$_1$ is alkenyl.

In certain embodiments, the present invention relates to the aforementioned method and any of the attendant definitions, wherein R$_1$ is —CH=CH$_2$.

In certain embodiments, the present invention relates to the aforementioned method and any of the attendant definitions, wherein R$_4$ is hydrogen or ether.

In certain embodiments, the present invention relates to the aforementioned method and any of the attendant definitions, wherein R$_4$ is hydrogen or —OCH$_3$.

In certain embodiments, the present invention relates to the aforementioned method and any of the attendant definitions, wherein R$_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein R$_1$ is —CH=CH$_2$; m is 0; n is 0; R$_4$ is hydrogen or —OCH$_3$; R$_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein R$_1$ is —CH=CH$_2$; m is 0; n is 0; R$_4$ is —OCH$_3$; R$_5$ is hydrogen; and R is —C(=S)N(H)-(4-t-Bu-Ph).

In certain embodiments, the present invention relates to the aforementioned method and any of the attendant definitions, wherein R$_1$ is —CH=CH$_2$; m is 0; n is 0; R$_4$ is —OCH$_3$; R$_5$ is hydrogen; and R is —C(=S)N(H)-(2-i-Pr-Ph).

In certain embodiments, the present invention relates to the aforementioned method and any of the attendant definitions, wherein R$_1$ is —CH=CH$_2$; m is 0; n is 0; R$_4$ is —OCH$_3$; R$_5$ is hydrogen; and R is —C(=S)N(H)-(Ph).

In certain embodiments, the present invention relates to the aforementioned method and any of the attendant definitions, wherein R$_1$ is —CH=CH$_2$; m is 0; n is 0; R$_4$ is —OCH$_3$; R$_5$ is hydrogen; and R is —C(=S)N(H)-(3,5-bisCF$_3$-Ph).

In certain embodiments, the present invention relates to the aforementioned method and any of the attendant definitions, wherein R$_1$ is —CH=CH$_2$; m is 0; n is 0; R$_4$ is hydrogen; R$_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

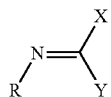

wherein
R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph-, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F:

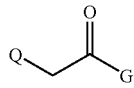

wherein

Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

One aspect of the present invention relates to a method of preparing a chiral, non-racemic β-amino β-cyano ketone, chiral, non-racemic β-amino β-keto ester, chiral, non-racemic β-amino β-cyano ester or chiral, non-racemic β-amino 1,3-diketone, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula IV:

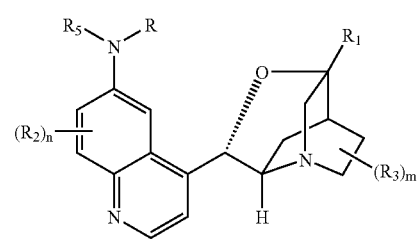

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6$(R')$_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6$(R')$_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(4-t-Bu-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(2-i-Pr-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

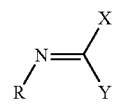

E wherein

R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F:

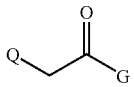

wherein
Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

Methods of Invention—Kinetic Resolutions

In another aspect of the present invention, a kinetic resolution of enantiomers or diastereomers of the substrate or the nucleophile is catalyzed by a subject non-racemic, chiral catalyst. For example, in the subject kinetic resolution processes for a racemic substrate, when the transformation is complete or interrupted one enantiomer can be preferentially recovered as unreacted substrate while the other has been preferentially transformed to the desired product. In other words, the kinetic resolution of the substrate can be performed to provide the desired enantiomer or diastereomer of the product. Of course, it will be appreciated that the kinetic resolution of the substrate can also be performed by removing the undesired enantiomer by reaction with a nucleophile, and recovering the desired enantiomer of the substrate unchanged from the reaction mixture. Likewise, the kinetic resolution of the nucleophile can be performed by removing the undesired enantiomer by reaction with a substrate, and recovering the desired enantiomer of the nucleophile unchanged from the reaction mixture. One significant advantage of kinetic resolutions is the ability to use inexpensive racemic starting materials rather than expensive, enantiomerically pure starting compounds.

In the non-dynamic kinetic resolution methods, as applied to a racemic substrate, one enantiomer can be recovered as unreacted substrate while the other is transformed to the desired product. Of course, one of ordinary skill in the art will recognize that the desired product of a kinetic resolution can be the enantiomer or diastereomer that reacts, the enantiomer or diastereomer that does not react, or both. One significant advantage of the methods of the present invention is the ability to use inexpensive racemic or diastereomeric mixtures of the starting materials, rather than expensive, enantiomerically or diastereomerically pure starting compounds.

The methods can also be applied to dynamic kinetic resolutions, e.g., wherein the yield of the enantiomerically or diastereomerically pure product from a kinetic resolution of a racemic substrate exceeds 50% due to in situ equilibration of the enantiomers or diastereomers of the substrate prior to the catalyzed attack of the nucleophile. Dynamic kinetic resolution methods are preferred for this reason.

In certain embodiments, the present invention relates to a method of performing a kinetic resolution of a racemic mixture or a diastereomeric mixture of a chiral substrate, comprising the step of combining a racemic mixture or a diastereomeric mixture of a chiral substrate with a nucleophile, in the presence of a chiral, non-racemic catalyst, wherein said chiral non-racemic catalyst catalyzes the addition of said nucleophile to said chiral substrate to give a chiral product or unreacted chiral substrate or both enriched in one enantiomer or diastereomer. In certain embodiments, the present invention relates to the aforementioned method of performing a kinetic resolution, wherein said kinetic resolution is dynamic.

Kinetic Resolution of Enolates via Asymmetric Addition to Electron-Deficient Alkenes One aspect of the present invention relates to a method of kinetic resolution, comprising the step of:

reacting a racemic β-cyano ketone, racemic β-keto ester, racemic β-cyano ester, or racemic 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula I:

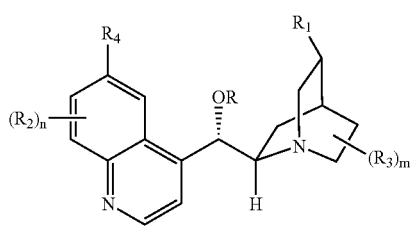

wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and $R_1$ is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and $R_1$ is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=$CH_2$; m is 0; and n is 0.

In certain embodiments, the present invention relates to the aforementioned method and any of the attendant definitions, wherein R is diazene; $R_1$ is —CH=$CH_2$; m is 0; and n is 0.

In certain embodiments, the present invention relates to the aforementioned method and any of the attendant definitions, wherein R is halobenzoyl; $R_1$ is —CH=$CH_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=$CH_2$; m is 0; and n is 0.

In certain embodiments, the present invention relates to the aforementioned method and any of the attendant definitions, wherein R represents 4-chlorobenzoyl; $R_1$ is —CH=$CH_2$; m is 0; and n is 0.

In certain embodiments, the present invention relates to the aforementioned method and any of the attendant definitions, wherein said electron-deficient alkene is represented by C:

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said racemic β-cyano ketone, racemic β-keto ester, racemic β-cyano ester, or racemic 1,3-diketone is represented by E:

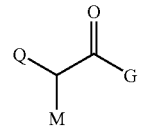

E wherein

M represents alkyl, aryl, heteroaryl, aralkyl, or heteroaralkyl;

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and M represents alkyl or aralkyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and Q represents cyano.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; M represents alkyl or aralkyl; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 40 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 10 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 5 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

In certain embodiments, the present invention relates to the aforementioned method and any of the attendant definitions, wherein when said method is completed or interrupted the unreacted β-cyano ketone, β-keto ester, β-cyano ester or 1,3-diketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted β-cyano ketone, β-keto ester, β-cyano ester or 1,3-diketone is racemic, and the enantiomeric excess or diastereomeric excess of the product is greater than zero.

One aspect of the present invention relates to a method of kinetic resolution, comprising the step of:

reacting a racemic β-cyano ketone, racemic β-keto ester, racemic β-cyano ester, or racemic 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula II:

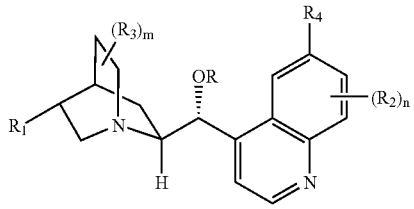

wherein, independently for each occurrence:

R represents substituted or unsubstituted aryl, heteroaryl, aralkyl, heteroaralkyl, arylcarbonyl, or heteroarylcarbonyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH.

In certain embodiments, the present invention relates to the aforementioned method and any of the attendant definitions, wherein R represents phenanthrene.

In certain embodiments, the present invention relates to the aforementioned method and any of the attendant definitions, wherein R represents substituted or unsubstituted diazene.

In certain embodiments, the present invention relates to the aforementioned method and any of the attendant definitions, wherein R represents 5-chloro-3,6-diphenyl-2,4-diazene.

In certain embodiments, the present invention relates to the aforementioned method and any of the attendant definitions, wherein R represents halobenzoyl.

In certain embodiments, the present invention relates to the aforementioned method and any of the attendant definitions, wherein R represents 4-chlorobenzoyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is diazene and $R_1$ is ethyl.

In certain embodiments, the present invention relates to the aforementioned method and any of the attendant definitions, wherein R is halobenzoyl and $R_1$ is ethyl.

In certain embodiments, the present invention relates to the aforementioned method and any of the attendant definitions, wherein R represents 5-chloro-3,6-diphenyl-2,4-diazene; and $R_1$ is ethyl.

In certain embodiments, the present invention relates to the aforementioned method and any of the attendant definitions, wherein R represents 4-chlorobenzoyl; and $R_1$ is ethyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is diazene and $R_1$ is —CH=$CH_2$.

In certain embodiments, the present invention relates to the aforementioned method and any of the attendant definitions, wherein R is halobenzoyl and $R_1$ is —CH=$CH_2$.

In certain embodiments, the present invention relates to the aforementioned method and any of the attendant definitions, wherein R represents 5-chloro-3,6-diphenyl-2,4-diazene; and $R_1$ is —CH=$CH_2$.

In certain embodiments, the present invention relates to the aforementioned method and any of the attendant definitions, wherein R represents 4-chlorobenzoyl; and $R_1$ is —CH=$CH_2$.

In certain embodiments, the present invention relates to the aforementioned method and any of the attendant definitions, wherein R is phenanthrene; $R_1$ is ethyl; m is 0; and n is 0.

In certain embodiments, the present invention relates to the aforementioned method and any of the attendant definitions, wherein R is diazene; $R_1$ is ethyl; m is 0; and n is 0.

In certain embodiments, the present invention relates to the aforementioned method and any of the attendant definitions, wherein R is halobenzoyl; $R_1$ is ethyl; m is 0; and n is 0.

In certain embodiments, the present invention relates to the aforementioned method and any of the attendant definitions, wherein R represents 5-chloro-3,6-diphenyl-2,4-diazene; $R_1$ is ethyl; m is 0; and n is 0.

In certain embodiments, the present invention relates to the aforementioned method and any of the attendant definitions, wherein R represents 4-chlorobenzoyl; $R_1$ is ethyl; m is 0; and n is 0.

In certain embodiments, the present invention relates to the aforementioned method and any of the attendant definitions, wherein R is phenanthrene; $R_1$ is —CH=$CH_2$; m is 0; and n is 0.

In certain embodiments, the present invention relates to the aforementioned method and any of the attendant definitions, wherein R is diazene; $R_1$ is —CH=$CH_2$; m is 0; and n is 0.

In certain embodiments, the present invention relates to the aforementioned method and any of the attendant definitions, wherein R is halobenzoyl; $R_1$ is —CH=$CH_2$; m is 0; and n is 0.

In certain embodiments, the present invention relates to the aforementioned method and any of the attendant definitions, wherein R represents 5-chloro-3,6-diphenyl-2,4-diazene; $R_1$ is —CH=$CH_2$; m is 0; and n is 0.

In certain embodiments, the present invention relates to the aforementioned method and any of the attendant definitions, wherein R represents 4-chlorobenzoyl; $R_1$ is —CH=$CH_2$; m is 0; and n is 0.

In certain embodiments, the present invention relates to the aforementioned method and any of the attendant definitions, wherein said electron-deficient alkene is represented by C:

wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said racemic β-cyano ketone, racemic β-keto ester, racemic β-cyano ester, or racemic 1,3-diketone is represented by E:

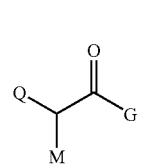

wherein

M represents alkyl, aryl, heteroaryl, aralkyl, or heteroaralkyl;

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and M represents alkyl or aralkyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and Q represents cyano.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said racemic β-cyano ketone, racemic β-keto ester, racemic β-cyano ester, or racemic 1,3-diketone is represented by E; M represents alkyl or aralkyl; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 40 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 10 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said catalyst is present in less than about 5 mol % relative to said racemic β-cyano ketone, racemic β-keto ester, racemic β-cyano ester, or racemic 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

In certain embodiments, the present invention relates to the aforementioned method and any of the attendant definitions, wherein when said method is completed or interrupted the unreacted β-cyano ketone, β-keto ester, β-cyano ester or 1,3-diketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted β-cyano ketone, β-keto ester, β-cyano ester or 1,3-diketone is racemic, and the enantiomeric excess or diastereomeric excess of the product is greater than zero.

One aspect of the present invention relates to a method of kinetic resolution, comprising the step of:

reacting a racemic β-cyano ketone, racemic β-keto ester, racemic β-cyano ester, or racemic 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

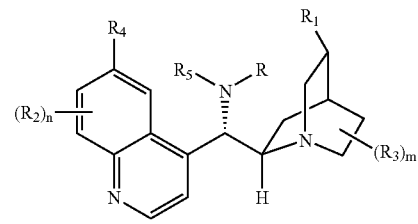

wherein, independently for each occurrence:

$R$ represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

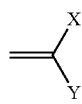

wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

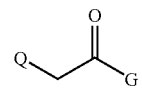

wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

In certain embodiments, the present invention relates to the aforementioned method and any of the attendant definitions, wherein when said method is completed or interrupted the unreacted β-cyano ketone, β-keto ester, β-cyano ester or 1,3-diketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted β-cyano ketone, β-keto ester, β-cyano ester or 1,3-diketone is racemic, and the enantiomeric excess or diastereomeric excess of the product is greater than zero.

One aspect of the present invention relates to a method of kinetic resolution, comprising the step of:

reacting a racemic β-cyano ketone, racemic β-keto ester, racemic β-cyano ester, or racemic 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

IV wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

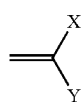

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

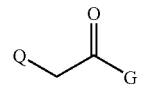

D wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

In certain embodiments, the present invention relates to the aforementioned method and any of the attendant definitions, wherein when said method is completed or interrupted the unreacted β-cyano ketone, β-keto ester, β-cyano ester or 1,3-diketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted β-cyano ketone, β-keto ester, β-cyano ester or 1,3-diketone is racemic, and the enantiomeric excess or diastereomeric excess of the product is greater than zero.

One aspect of the present invention relates to a method of kinetic resolution, comprising the step of:

reacting a racemic β-cyano ketone, racemic β-keto ester, racemic β-cyano ester, or racemic 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula V:

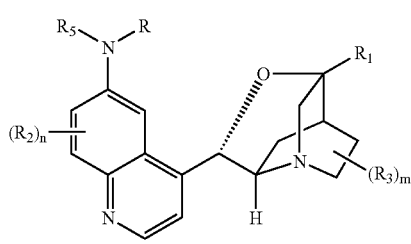

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(4-t-Bu-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(2-i-Pr-Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(Ph).

In certain embodiments, the present invention relates to the aforementioned method and any of the attendant definitions, wherein $R_1$ is —CH$_2$CH$_3$; m is 0; n is 0; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —$CH_2CH_3$; m is 0; n is 0; $R_5$ is hydrogen; and R is —C(=S)N(H)-(3,5-bisCF$_3$-Ph).

In certain embodiments, the present invention relates to the aforementioned method and any of the attendant definitions, wherein said electron-deficient alkene is represented by C:

C wherein

X represents fluorine, chlorine, bromine, or iodine; and

Y represents cyano, nitro, alkyl ester, aryl ester, heteroaryl ester, aralkyl ester, heteroaralkyl, alkylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said electron-deficient alkene is represented by C; and X represents chlorine.

In certain embodiments, the present invention relates to the aforementioned method and any of the attendant definitions, wherein said electron-deficient alkene is represented by C; and Y represents cyano.

In certain embodiments, the present invention relates to the aforementioned method and any of the attendant definitions, wherein said electron-deficient alkene is represented by C; X represents chlorine; and Y represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D:

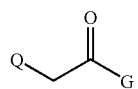

D wherein

Q represents cyano, alkylcarbonyl, arylcarbonyl, heteroarylcarbonyl, aralkylcarbonyl, or heteroaralkylcarbonyl; and G represents alkyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and Q represents cyano.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by D; Q represents cyano; and G represents alkyl, aryl, heteroaryl, aralkyl, heteroaralkyl, alkoxyl, or aralkoxyl.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 50%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 70%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 90%.

In certain embodiments, the present invention relates to the aforementioned method and any of the attendant definitions, wherein said chiral, non-racemic β-cyano ketone, chiral, non-racemic β-keto ester, chiral, non-racemic β-cyano ester or chiral, non-racemic 1,3-diketone has an enantiomeric excess or diastereomeric excess greater than about 95%.

In certain embodiments, the present invention relates to the aforementioned method and any of the attendant definitions, wherein when said method is completed or interrupted the unreacted β-cyano ketone, β-keto ester, β-cyano ester or 1,3-diketone is not racemic, and the enantiomeric excess or diastereomeric excess of the product is greater than zero.

In certain embodiments, the present invention relates to the aforementioned method and any of the attendant definitions, wherein when said method is completed or interrupted, the unreacted β-cyano ketone, β-keto ester, β-cyano ester or 1,3-diketone is racemic, and the enantiomeric excess or diastereomeric excess of the product is greater than zero.

Kinetic Resolution of Enolates Via Asymmetric Addition to Imines

One aspect of the present invention relates to a method of kinetic resolution, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula III:

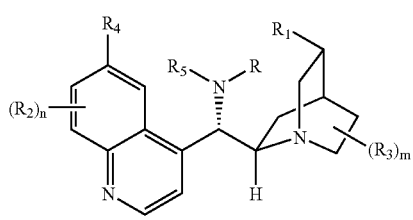

III wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

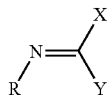

wherein

R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-yano ester, or prochiral 1,3-diketone is represented by F:

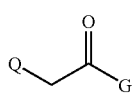

wherein

Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 90%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 95%.

One aspect of the present invention relates to a method of kinetic resolution, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula IV:

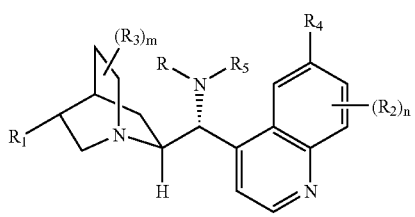

wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—$C_6(R')_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—$C_6(R')_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein $R_4$ is hydrogen or ether.

In certain embodiments, the present invention relates to the aforementioned method and any of the attendant definitions, wherein $R_4$ is hydrogen or —OCH$_3$.

In certain embodiments, the present invention relates to the aforementioned method and any of the attendant definitions, wherein $R_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein $R_1$ is —CH=CH$_2$; m is 0; n is 0; $R_4$ is hydrogen or —OCH$_3$; $R_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(4-t-Bu-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(2-i-Pr-Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(Ph).

In certain embodiments, the present invention relates to the aforementioned method and any of the attendant definitions, wherein $R_1$ is —CH=CH$_2$; m is 0; n is 0; $R_4$ is —OCH$_3$; $R_5$ is hydrogen; and R is —C(=S)N(H)-(3,5-bisCF$_3$-Ph).

In certain embodiments, the present invention relates to the aforementioned method and any of the attendant definitions, wherein $R_1$ is —CH=CH$_2$; m is 0; n is 0; $R_4$ is hydrogen; $R_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

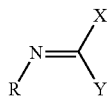

wherein

R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F:

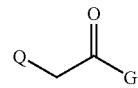

wherein

Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 90%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 95%.

One aspect of the present invention relates to a method of kinetic resolution, comprising the step of:

reacting a prochiral β-cyano ketone, prochiral β-keto ester, prochiral β-cyano ester, or prochiral 1,3-diketone with an imine in the presence of a catalyst; thereby producing a chiral, non-racemic β-amino β-cyano ketone, chiral, non-racemic β-amino β-keto ester, chiral, non-racemic β-amino β-cyano ester or chiral, non-racemic β-amino 1,3-diketone; wherein said catalyst is represented by formula IV:

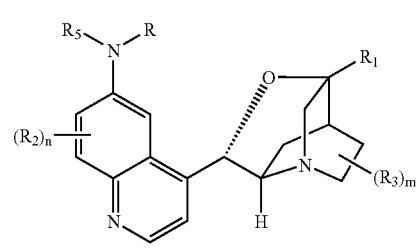

V wherein, independently for each occurrence:

R represents H or a substituted or unsubstituted alkyl, alkenyl, alkynyl, aryl, aralkyl, heteroaryl, heteroaralkyl, heterocyclic, heterocycloalkyl, —C(=O)-alkyl, —C(=O)-alkenyl, —C(=O)-alkynyl, —C(=O)-aryl, —C(=O)-aralkyl, —C(=O)-heteroaryl, —C(=O)-heteroaralkyl, —C(=O)-heterocyclic, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

R$_1$ represents a substituted or unsubstituted alkyl or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_5$ represents H or lower alkyl;

n is an integer from 0 to 6 inclusive; and m is an integer from 0 to 8 inclusive.

In certain embodiments, the present invention relates to the aforementioned method and any of the attendant definitions, wherein R is —C(=S)N(H)-aryl.

In certain embodiments, the present invention relates to the aforementioned method and any of the attendant definitions, wherein R is —C(=S)N(H)-monocyclic aryl.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, and ester.

In certain embodiments, the present invention relates to the aforementioned method and any of the attendant definitions, wherein R is —C(=S)N(H)—C$_6$(R')$_6$; and R' is independently for each occurrence selected from the group consisting of hydrogen, lower alkyl, and lower fluoroalkyl.

In certain embodiments, the present invention relates to the aforementioned method and any of the attendant definitions, wherein R is —C(=S)N(H)-(4-t-Bu-Ph), —C(=S)N(H)-(2-i-Pr-Ph), —C(=S)N(H)-(2-i-Pr-Ph), —C(=S)N(H)-(Ph), and —C(=S)N(H)-(3,5-bisCF$_3$-Ph).

In certain embodiments, the present invention relates to the aforementioned method and any of the attendant definitions, wherein R$_1$ is alkyl.

In certain embodiments, the present invention relates to the aforementioned method and any of the attendant definitions, wherein R$_1$ is ethyl.

In certain embodiments, the present invention relates to the aforementioned method and any of the attendant definitions, wherein R$_1$ is alkenyl.

In certain embodiments, the present invention relates to the aforementioned method and any of the attendant definitions, wherein R$_1$ is —CH=CH$_2$.

In certain embodiments, the present invention relates to the aforementioned method and any of the attendant definitions, wherein R$_5$ is hydrogen.

In certain embodiments, the present invention relates to the aforementioned method and any of the attendant definitions, wherein m is 0.

In certain embodiments, the present invention relates to the aforementioned method and any of the attendant definitions, wherein n is 0.

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(4-t-Bu-Ph), —C(=S)N(H)-(2-i-Pr-Ph), —C(=S)N(H)-(Ph), or —C(=S)N(H)-(3,5-bisCF$_3$-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(4-t-Bu-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(2-i-Pr-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(3,5-bisCF$_3$-Ph).

In certain embodiments, the present invention relates to the aforementioned method and any of the attendant definitions, wherein R$_1$ is —CH$_2$CH$_3$; m is 0; n is 0; R$_5$ is hydrogen; and R is —C(=S)N(H)-(3,5-bisCF$_3$-Ph).

In certain embodiments, the present invention relates to the aforementioned method and any of the attendant definitions, wherein said imine is represented by E:

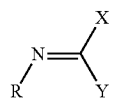

E wherein

R represents hydrogen, alkyl, alkenyl, alkynyl, aryl, heteroaryl, aralkyl, heteroaralkyl, alkylcarbonyl, arylcarbonyl, heteroarylcarbonyl, aralkylcarbonyl, heteroaralkylcarbonyl, alkyloxycarbonyl, aryloxycarbonyl, heteroaryloxycarbonyl, aralkyloxycarbonyl, or heteroaralkyloxycarbonyl;

X represents hydrogen, alkyl, alkenyl, alkynyl, aryl, heteroaryl, aralkyl, or heteroaralkyl; and Y represents alkyl, alkenyl, alkynyl, aryl, heteroaryl, aralkyl, or heteroaralkyl.

In certain embodiments, the present invention relates to the aforementioned method and any of the attendant definitions, wherein said imine is represented by E; and R represents alyl or alkyloxycarbonyl.

In certain embodiments, the present invention relates to the aforementioned method and any of the attendant definitions, wherein said imine is represented by E; and R represents t-butyloxycarbonyl.

In certain embodiments, the present invention relates to the aforementioned method and any of the attendant definitions, wherein said imine is represented by E; and X represents alkyl, aryl, or heteroaryl.

In certain embodiments, the present invention relates to the aforementioned method and any of the attendant definitions, wherein said imine is represented by E; and X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-.

In certain embodiments, the present invention relates to the aforementioned method and any of the attendant definitions, wherein said imine is represented by E; and Y represents hydrogen.

In certain embodiments, the present invention relates to the aforementioned method and any of the attendant definitions, wherein said imine is represented by E; R represents t-butyloxycarbonyl; X represents 2-Me-Ph-, 3-Me-Ph, 4-Me-Ph, 4-F-Ph-, 4-Cl-Ph-, 4-CF$_3$-Ph-, 2-furyl-, 2-thienyl-, 4-OCH$_3$-Ph-, 3,4-OCH$_3$O-Ph-, 3-vinyl-Ph-, CH$_3$CH$_2$—, CH$_3$CH$_2$CH$_2$CH$_2$—, cyclohexyl-, or Ph-; and Y represents hydrogen.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F:

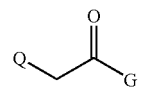

F wherein

Q represents cyano, alkylcarbonyl, alkenylcarbonyl, alkynylcarbonyl, arylcarbonyl, heteroarylcarbonyl, aralkylcarbonyl, or heteroaralkylcarbonyl; and G represents alkyl, alkenyl, alkynyl, aryl, heteroaryl, aralkyl, heteroaralkyl, alkoxyl, aryloxyl, heteroaryloxyl, aralkoxyl, heteroaralkoxyl, alkylamino, arylamino, aralkylamino, or heteroaralkylamino.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, alkynylcarbonyl, arylcarbonyl, heteroarylcarbonyl, aralkylcarbonyl, or heteroaralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents alkylcarbonyl, alkenylcarbonyl, or, aralkylcarbonyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$, —C(=O)CH$_2$CH$_2$=CH$_2$, or, —CH$_2$Ph.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents alkyloxy, aralkyloxy or alkenyloxy.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and G represents methyl, benzyl or allyl.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_3$; and G represents —CH$_3$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$CH$_2$=CH$_2$; and G represents —CH$_2$CH$_2$=CH$_2$.

In certain embodiments, the present invention relates to the aforementioned method and any of the attendant definitions, wherein said prochiral β-cyano ketone, prochiral β-keto ester, prochiral β-cyano ester, or prochiral 1,3-diketone is represented by F; and Q represents —C(=O)CH$_2$Ph; and G represents —CH$_2$Ph.

In certain embodiments, the present invention relates to the aforementioned method and any of the attendant definitions, wherein said catalyst is present in less than about 70 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 40 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 10 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said catalyst is present in less than about 5 mol % relative to said prochiral β-cyano ketone, prochiral β-keto ester, prochiral β-cyano ester, or prochiral 1,3-diketone.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 50%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 70%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 90%.

In certain embodiments, the present invention relates to the aforementioned method and any of the attendant definitions, wherein said chiral, non-racemic β-amino β-cyano ketone, chiral, non-racemic β-amino β-keto ester, chiral, non-racemic β-amino β-cyano ester or chiral, non-racemic β-amino 1,3-diketone has an enantiomeric excess or diastereomeric excess greater than about 95%.

Nucleophiles

Nucleophiles which are useful in the present invention may be determined by the skilled artisan according to several criteria. Suitable nucleophiles can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles, such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art. For nucleophiles which exist as anions, the counterion can be any of a variety of conventional cations, including alkali and alkaline earth metal cations and ammonium cations. In certain embodiments, the nucleophile may be part of the substrate, thus resulting in an intramolecular reaction.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least one reactive electrophilic center or moiety with distinct stereogenic faces. The catalyzed, stereoselective attack of the nucleophile at the electrophilic center will produce a chiral non-racemic product. Most of the substrates contemplated for use in the methods of the present invention contain at least one carbonyl moiety. Examples of suitable carbonyl-containing substrates which are susceptible to nucleophilic attack by the subject method include ketones, aldehydes, aldehyde-ketones, diketones, keto-esters, aldehyde-esters, and the like.

In other embodiments, the electrophilic substrate will be a chiral compound. In certain embodiments, the substrate will be a racemic mixture. In certain embodiments, the substrate will be a mixture of diastereomers. In certain embodiments, the methods of the present invention effect a kinetic resolution. In certain embodiments, the methods of the present invention effect a dynamic kinetic resolution.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some certain embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

General Information $^1$H and $^{13}$C NMR spectra were recorded on a Varian instrument (400 MHz and 100 MHz, respectively) and internally referenced to tetramethylsilane signal or residual protic solvent signals. Data for $^1$H NMR are recorded as follows: chemical shift (δ, ppm), multiplicity (s, singlet; d, doublet; t, triplet; q, quartet; m, multiplet), integration, coupling constant (Hz). Data for $^{13}$C NMR are reported in terms of chemical shift (δ, ppm). Infrared spectra were recorded on a Perkin Elmer FT-IR Spectrometer and are reported in frequency of absorption. Low resolution mass spectra for all the new compounds done by either 20 eV, $CH_4$/CI or $NH_3$/CI were recorded on a Hewlett-Packard 5989A GC/MS, and exact mass spectra on a VG 7070 high resolution mass spectrometer. Specific rotations were measured on a Jasco Digital Polarimeter.

High pressure liquid chromatography (HPLC) analysis was performed on a Hewlett-Packard 1100 Series instrument equipped with a quaternary pump, using a Daicel Chiralpak OD, Column (250×4.6 mm) or Regis (R,R)Whelk-O1 Reversible Column (250×4.6 mm). UV detection was monitored at 220 nm or at 254 nm.

Example 1

Preparation of Quinidine 9-O-(9'-Phenanthryl) Ether, QD-PHN

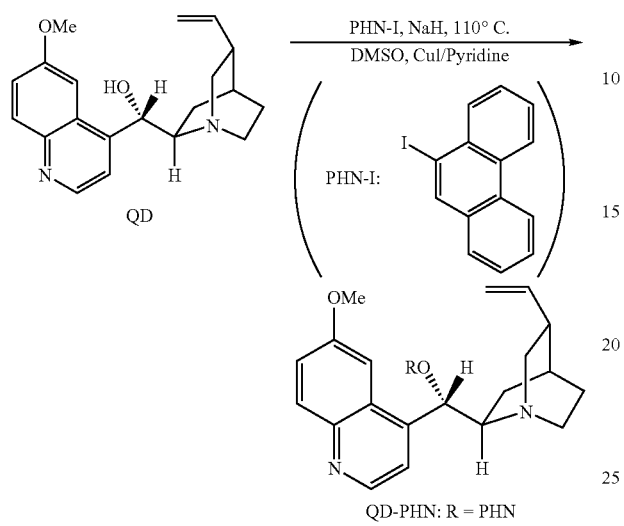

QD-PHN: R = PHN

A 500 mL three-necked round-bottomed flask equipped with a mechanical stirrer, reflux condenser, and inert gas in- and outlet was charged with quinidine (QD-1, 12.8 g, 39.5 mmol, 1.2 eq). The flask was flushed for 30 min with a gentle stream of argon. Anhydrous dimethyl sulfoxide (130 mL, freshly distilled in presence of $CaH_2$) was added, and the reaction mixture was stirred at room temperature until all the quinidine was dissolved. Sodium hydride (60% oil dispersion, 2.0 g, 1.5 eq.) was added in small portions yielding an orange, slightly cloudy solution of the corresponding sodium alkoxide. Upon addition of pyridine (6.4 mL, 2.4 eq.) and copper(I) iodide (7.8 g, 1.2 eq.) to the reaction mixture at room temperature, the color of the reaction mixture was changed from orange to dark green. After 30 min all of the precipitate dissolved, and a clear solution was formed. 9-iodophenanthrene (10.0 g, 32.9 mmol), was added, and the reaction mixture was kept at 113° C. for 70 h (oil bath, temperature: 120° C.). The reaction mixture was allowed to cool to room temperature. Water (100 mL), methylene chloride (100 mL), and diethyl ether (100 mL) were successively added to the brown solution followed by ethylenediaminetetraacetate disodium salt dehydrate (20 g) and concentrated aqueous ammonia solution (20 mL, 29%, w/w). The argon inlet was removed, and a gentle stream of air was flushed through the well-agitated reaction mixture for about 1 h. The reaction mixture was transferred to a separatory funnel and the turquoise blue aqueous phase separated from the dark brown organic phase. The aqueous layer was washed twice with methylene chloride (100 mL), and the combined organic phases were extracted three times with aqueous ammonia solution (200 mL, 5%, w/w) until the aqueous phase remained colorless. Then the organic layer was washed with HCl aq (1 N 2×50 mL) twice and washed with $H_2O$ three times (3×50 mL) to remove the left QD. The organic layer was washed with $NH_4OH$ to neutralize the salt and dried over $Na_2SO_4$ and the solvent was removed in vacuo to yield the crude product. The crude product was dissolved in ethyl ether (300 mL) and treated with HCl (1N in $Et_2O$) until no further precipitates was generated. The precipitates were collected and dissolved in $CH_2Cl_2$ and basified with $NH_4OH$ and dried over $Na_2SO_4$ and the solvent in vacuo to give yellowish foam QD-PHN (5.6 g, 66% yield). $[\alpha]_D^{23}=+310.7$(C 0.89 EtOH) $^1$HNMR (CDCl$_3$, 400 Hz) δ 8.65-8.71(m, 2H), 8.61(d, J=4.8 Hz, 1H), 8.52(d, J=8 Hz, 1H), 8.07(d, J=9.2 Hz, 1H), 7.70-7.75(m, 2H), 7.55(d, J=2.4 Hz, 1H), 7.38-7.46(m, 5H), 6.66 (s, 1H), 6.35(br, H), 6.12-6.21(m, 1H), 5.18(d, J=10.4 Hz, 1H), 5.12(m, 1H), 4.03(s, 3H), 3.32-3.42(m, 2H), 2.97-3.06 (m, 2H), 2.79-2.87(m, 1H), 2.44-2.50(t, J=10 Hz, 1H), 2.34-3.25(m, 1H), 1.97(br, 1H), 1.55-1.62(m, 3H). $^{13}$CNMR: (CDCl$_3$, 100 Hz): 158.1, 150.4, 147.71, 144.7, 143.7, 140.3, 132.3, 132.2, 131.5, 127.5, 127.3, 126.8, 126.7, 126.6, 126.4, 124.5, 122.8, 122.7, 122.3, 121.8, 118.2, 114.7, 104.8, 100.8, 78.8, 60.5, 55.8, 50.2, 49.9, 39.6, 27.8, 26.5, 22.1. IR: 3062, 2935, 2863, 1622, 1594, 1507, 1454, 1226, 1117, 750.

Example 2

Preparation of Quinidine 9-O-Benzyl Ether, QD-OBn

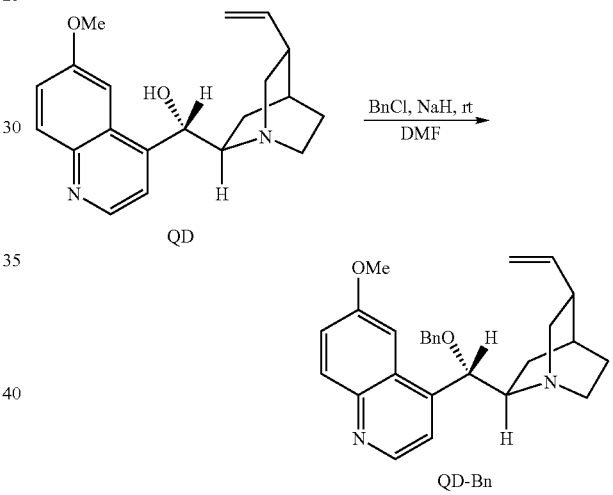

To the solution of QD (2.0 g, 6.2 mmol) in DMF (20 mL, freshly distilled from the suspension of $CaH_2$ in DMF) was added NaH (0.68 g, 57% suspension in mineral oil, 2.5 eq.) and let it stirred at rt for 2 h. Then BnCl (0.78 mL, 1.1 eq.) was added dropwise through syringe in 10 minutes and let it stir overnight. When the reaction was done, the brine was added carefully (20 mL) and the resulting mixture was extracted with ethyl acetate (100 mL). The organic phase was washed with brine (3×50 mL) and dried over $Na_2SO_4$. The solvent was removed in vacuo and purified by flash chromatography (MeOH/Ethyl acetate: 1/40) to give a yellowish oil (2.3 g, 90% yield). $^1$HNMR (400 MHz, CDCl$_3$) δ: 8.77 (d, J=5.2 Hz, 1H), 8.05 (d, J=9.2 Hz, 1H), 7.49 (d, J=4.0 Hz, 1H), 7.40-7.31 (m, 7H), 6.00-5.92 (m, 1H), 5.23 (br, 1H), 5.02-5.00 (m, 1H), 4.97 (s, 1H), 4.49-4.37 (AB, 2H), 3.90 (s, 3H), 3.26(m, 1H), 3.09-3.08 (m, 1H), 2.93-2.71 (m, 3H), 2.26-2.22 (m, 1H), 2.11-2.05 (m, 1H), 1.75 (br, 1H), 1.51-1.43 (m, 2H), 1.29-1.24 (m, 1H). $^{13}$CNMR (100 Hz, CDCl$_3$) δ 157.8, 147.6, 144.7, 137.8, 31.9, 128.4, 128.0, 127.8, 127.5, 121.9, 119.1, 114.5, 101.2, 71.3, 60.1, 55.7, 50.1, 49.4, 40.0, 28.1, 26.4.

Example 3

General Procedure for the Preparation of QD-4a, QD-4b, QD-4c and Q-4a

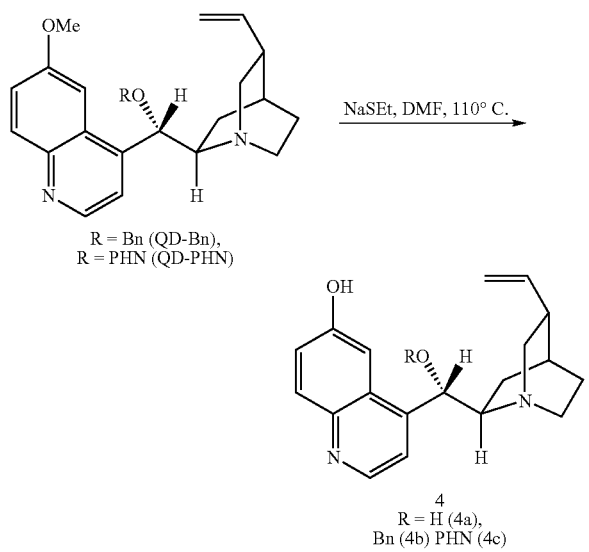

Under $N_2$ atmosphere, a suspension of QD (8.0 mmol) in dry DMF (50 mL, freshly distilled from the suspension of $CaH_2$ in DMF) was heated at 110° C. for 4-6 hours until a TLC analysis showed that QD was completely consumed. The reaction mixture was cooled down to room temperature, then mixed with sat. $NH_4Cl$ (40 mL) and $H_2O$ (50 mL) and monitored by pH paper till pH=7. The resulting mixture was extracted with Ethyl Acetate (2×200 mL), the organic phase was washed with brine (4×50 mL), dried over $Na_2SO_4$, and concentrated in vacuo. The residue was subjected to flash chromatography (Ethyl Acetate/MeOH/$NEt_3$ system) to afford the desired product.

QD-4a was obtained as a yellowish solid in 92% yield from quinidine. $[\alpha]_D^{25}$=+240.3 (c 1.13, EtOH); $^1$HNMR (400 MHz, $CD_3OD$) δ 8.58 (d, 1H, J=4.4 Hz), 7.88 (d, 1H, J=9.2 Hz), 7.62(d, 1H, J=5.2 Hz), 7.31 (dd, 1H, J=2.4 Hz, 9.2 Hz), 7.25 (d, 1H, J=2.4 Hz), 6.10-6.19 (m, 1H), 5.58 (d, 1H, J=2.8 Hz), 5.10 (d, 1H, J=18.8 Hz), 5.06 (d, 1H, J=10.4 Hz), 3.60 (ddd, 1H, J=2.0 Hz, 8.0 Hz, 13.6 Hz), 3.03 (dt, 1H, J=2.4 Hz, 9.2 Hz), 2.87-2.94(m, 2H), 2.74-2.82(m, 1H), 2.30 (dt, 1H, J=8.8 Hz, 8.4 Hz), 2.18-2.23 (m, 1H), 1.71 (br, 1H), 1.50-1.58 (m, 2H), 1.00-1.07 (m, 1H); $^{13}$CNMR (100 Hz, $CD_3OD$) δ 158.0, 149.8, 147.4, 143.9, 141.6, 131.4, 128.4, 123.3, 119.7, 115.2, 105.1, 72.2, 60.6, 50.8, 50.4, 41.3, 29.7, 27.0, 21.2; IR($CHCl_3$) v 3062, 2929, 2300-3500 (br), 1616, 1505, 1229, 739 cm$^{-1}$; HRMS (FAB) m/z calcd for ($C_{19}H_{22}N_2O_2$+H$^+$): 311.1760. found: 311.1755.

QD-4b was obtained as a yellowish powder in 87% yield from QD-Bn. $[\alpha]_D^{25}$=−138.9 (c 1.05, $CHCl_3$); $^1$HNMR (400 MHz, $CDCl_3$) δ 10.92 (br, 1H), 8.67 (d, J=4.4 Hz, 1H), 8.01(d, J=9.2 Hz, 1H), 7.86 (s, 1H), 7.44 (br, 1H), 7.35 (dd, J=2.4 Hz, 8.8 Hz, 1H), 7.24-7.28 (m, 5H), 5.97-5.89 (m, 1H), 5.53 (br, 1H), 4.97 (d, J=10.0 Hz, 1H), 4.94 (s, 1H), 4.34-4.25 (AB, 2H), 3.56 (br, 1H), 3.05-3.03 (m, 2H), 2.87-2.78 (m, 2H), 2.26-2.24 (m, 2H), 1.74 (br, 1H), 1.52-1.39 (m, 2H), 1.13 (br, 1H); $^{13}$CNMR (100 Hz, $CDCl_3$) δ 157.0, 146.5, 143.6, 139.9, 137.7, 131.3, 128.3, 127.9, 127.8, 127.7, 127.6, 123.4, 114.9, 106.7, 79.0, 71.2, 59.0, 49.7, 49.2, 39.6, 28.0, 25.9.

QD-4c was obtained as a yellowish solid in 91% yield from QD-PHN. $[\alpha]_D^{25}$=−304.6 (c 0.98, $CHCl_3$); $^1$HNMR (400 MHz, $CDCl_3$) δ 8.69-8.67 (m, 1H), 8.63-8.61 (m, 1H), 8,46 (d, J=8.0 Hz, 1H), 8.20 (d, 1H, J=2.0 Hz, 1H), 7.78 (d, J=9.2 Hz, 1H), 7.74-7.70 (m, 2H), 7.35 (d, J=5.2 Hz, 1H), 7.25-7.26 (m, 1H), 7.20 (t, J=7.2 Hz, 1H), 6.80 (t, J=7.2 Hz, 1H), 6.64 (s, 1H), 6.50 (d, J=7.2 Hz, 1H), 6.33(s, 1H), 6.23-6.15 (m, 1H), 5.27 (d, J=14.4 Hz, 1H), 5.12 (d, J=17.2 Hz, 1H), 3.58-3.53 (m, 1H), 3.36 (t, J=9.2 Hz, 1H), 3.09-2.99(m, 2H), 2.79-2.68 (m, 2H), 2.30-2.28 (m, 1H), 2.00 (br, 1H), 1.54-1.52 (m, 2H), 1.43-1.34 (m, 1H); $^{13}$CNMR (100 Hz, $CDCl_3$) δ157.0, 149.6, 146.9, 143.7, 142.4, 139.4, 131.9, 131.8, 131.5, 127.3, 127.2, 127.1, 126.6, 126.4, 126.3, 126.1, 124.5, 123.4, 122.8, 122.6, 121.9, 117.5, 115.3, 106.1, 105.0, 76.8, 59.2, 49.7, 49.5, 38.8, 27.4, 25.7, 20.3; IR($CHCl_3$) v 3300-2800 (br), 3070, 2939, 2870, 1622, 1506, 1455, 1225, 1115, 753 cm$^{-1}$;

Q-4a was obtained as a white solid in 80% yield from quinine. $[\alpha]_D^{25}$=−162.8 (c 0.93, EtOH); $^1$HNMR (400 MHz, $CD_3OD$) δ 8.58 (d, 1H, J=4.8 Hz), 7.89 (d, J=9.2 Hz, 1H), 7.61 (d, J=4.8 Hz, 1H), 7.32 (dd, J=2.4 Hz, 9.2 Hz, 1H), 7.28 (d, J=2.4 Hz, 1H), 5.69-5.78 (m, 1H), 5.51 (d, J=3.2 Hz, 1H), 4.95 (d, J=17.2 Hz, 1H), 4.88 (d, J=9.2 Hz, 1H), 3.66-3.73 (m, 1H), 3.05-3.13(m, 2H), 2.63-2.74 (m, 2H), 2.34 (br, 1H), 1.80-1.89 (m, 2H), 1.77-1.78 (m, 1H), 1.54-1.61(m, 1H), 1.39-1.46(m, 1H). $^{13}$CNMR (100 Hz, $CD_3OD$) δ 157.9, 149.8, 147.4, 144.0, 142.6, 131.4, 128.4, 123.3, 119.8, 115.0, 105.1, 72.2, 60.9, 57.6, 48.4, 44.2, 40.9, 29.2, 28.1, 21.8; IR($CHCl_3$) v 3055, 2937, 2870, 2300-3500(br), 1616, 1457, 1236, 1067 cm$^{-1}$; HRMS (FAB) m/z calcd. for ($C_{19}H_{22}N_2O_2$+H$^+$): 311.1760. found: 311.1761.

Example 4

General Procedure for the Asymmetric Conjugate Addition with Thiourea Catalysts

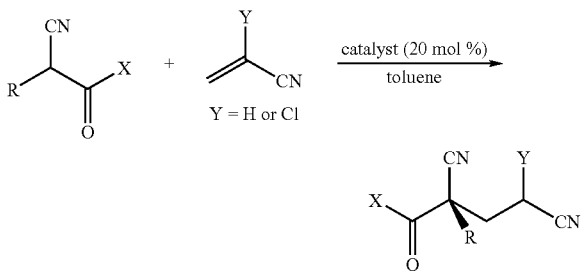

To a solution of α-cyanocarbonyl compound (0.2 mmol or 0.3 mmol) and thiourea catalyst (0.04 mmol or 0.03 mmol) in toluene (2 mL or 3 mL) was added acrylonitrile or 2-chloroacrylonitrile. The reaction mixture was kept at room temperature or 50° C. until α-cyanocarbonyl compound was completely consumed. The crude reaction mixture was filtered through a short plug of silica gel for the removal of the catalyst and washed with diethyl ether (5.0 mL). The filtrate was concentrated in vacuo, and the residue was subjected to flash chromatography on silica gel to give the pure adduct.

Example 5

Exemplary Procedure for Dehalogenation

Zinc (150 mg, 2.3 mmol, powder) was added to a solution of 3 (80.0 mg, 0.3 mmol) in diethyl ether (1.5 mL). To the resulting suspension, AcOH (1.5 mL) was added in one portion. The resulting mixture was stirred at room temperature for 24 h. Zinc powder was removed by silica gel-cotton plug and 4 was washed out from the plug by diethyl ether. The combined ether was washed with water, saturated $NaHCO_3$ and brine, dried over $Na_2SO_4$, concentrated to give colorless oil 4. Dinitrile 4 was diluted with diethyl ether and subjected to HPLC analysis directly.

INCORPORATION BY REFERENCE

U.S. patent application Ser. No. 11/140,574, filed May 27, 2005 is hereby incorporated by reference in its entirety. Moreover, all of the other U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula III:

wherein, independently for each occurrence:

R represents a substituted or unsubstituted alkenyl, alkynyl, aryl, aralkyl, heteroaryl, heteroaralkyl, heterocyclic, heterocycloalkyl, —C(═O)-alkyl, —C(═O)-alkenyl, —C(═O)-alkynyl, —C(═O)-heteroaralkyl, —C(═O)-heterocycloalkyl, —C(═S)N(H)-alkyl, —C(═S)N(H)-alkenyl, —C(═S)N(H)-alkynyl, —C(═S)N(H)-aryl, —C(═S)N(H)-aralkyl, —C(═S)N(H)-heteroaryl, —C(═S)N(H)-heteroaralkyl, —C(═S)N(H)-heterocyclic, or —C(═S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

2. A compound represented by formula IV:

wherein, independently for each occurrence:

R represents a substituted or unsubstituted alkenyl, alkynyl, aryl, aralkyl, heteroaryl, heteroaralkyl, heterocyclic, heterocycloalkyl, —C(═O)-atkyl, —C(═O)-alkenyl, —C(═O)-alkynyl, —C(═O)-heteroaralkyl, —C(═O)-heterocycloalkyl, —C(═S)N(H)-alkyl, —C(═S)N(H)-alkenyl, —C(═S)N(H)-alkynyl, —C(═S)N(H)-aryl, —C(═S)N(H)-aralkyl, —C(═S)N(H)-heteroaryl, —C(═S)N(H)-heteroaralkyl, —C(═S)N(H)-heterocyclic, or —C(═S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

3. The compound of claim 1 or 2, wherein R is —C(═S)N(H)-aryl.

4. The compound of claim 1 or 2, wherein R is —C(═S)N(H)-(4-t-Bu-Ph), —C(═S)N(H)-(2-i-Pr-Ph), —C(═S)N(H)-(2-i-Pr-Ph), —C(═S)N(H)-(Ph), and —C(S)N(H)-(3,5-bisCF_3-Ph).

5. The compound of claim 1 or 2, wherein $R_1$ is ethyl.

6. The compound of claim 1 or 2, wherein $R_1$ is —CH═CH_2.

7. The compound of claim 1 or 2, wherein $R_4$ is hydrogen or —$OCH_3$.

8. The compound of claim 1 or 2, wherein $R_5$ is hydrogen.

9. The compound of claim 1 or 2, wherein m is 0.

10. The compound of claim 1 or 2, wherein n is 0.

11. A method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

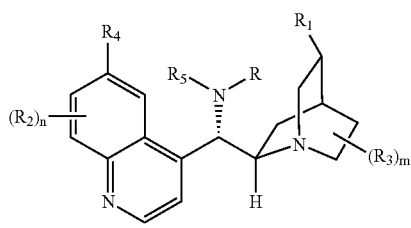

III wherein, independently for each occurrence:

R represents a substituted or unsubstituted alkenyl, alkynyl, aryl, aralkyl, heteroaryl, heteroaralkyl, heterocyclic, heterocycloalkyl, —C(=O)-atkyl, —C(=O)-alkenyl, —C(=O)-alkynyl, —C(=O)-heteroaralkyl, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

12. A method of preparing a chiral, non-racemic β- cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

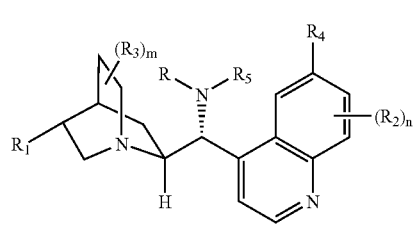

IV wherein, independently for each occurrence:

R represents a substituted or unsubstituted alkenyl, alkynyl, aryl, aralkyl, heteroaryl, heteroaralkyl, heterocyclic, heterocycloalkyl, —C(=O)-atkyl, —C(=O)-alkenyl, —C(=O)-alkynyl, —C(=O)-heteroaralkyl, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

13. A method of kinetic resolution comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

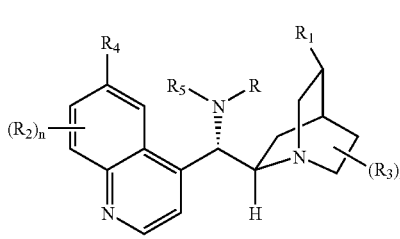

III wherein, independently for each occurrence:

R represents a substituted or unsubstituted alkenyl, alkynyl, aryl, aralkyl, heteroaryl, heteroaralkyl, heterocyclic, heterocycloalkyl, —C(=O)-atkyl, —C(=O)-alkenyl, —C(=O)-alkynyl, —C(=O)-heteroaralkyl, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

14. A method of kinetic resolution comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

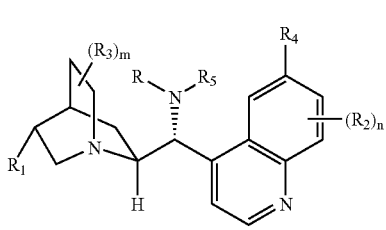

IV wherein, independently for each occurrence:

R represents a substituted or unsubstituted alkenyl, alkynyl, aryl, aralkyl, heteroaryl, heteroaralkyl, heterocyclic, heterocycloalkyl, —C(=O)-atkyl, —C(=O)-alkenyl, —C(=O)-alkynyl, —C(=O)-heteroaralkyl, —C(=O)-heterocycloalkyl, —C(=S)N(H)-alkyl, —C(=S)N(H)-alkenyl, —C(=S)N(H)-alkynyl, —C(=S)N(H)-aryl, —C(=S)N(H)-aralkyl, —C(=S)N(H)-heteroaryl, —C(=S)N(H)-heteroaralkyl, —C(=S)N(H)-heterocyclic, or —C(=S)N(H)-heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents H or lower alkyl;

n is an integer from 0 to 6 inclusive; and m is an integer from 0 to 8 inclusive.

15. A compound represented by formula III:

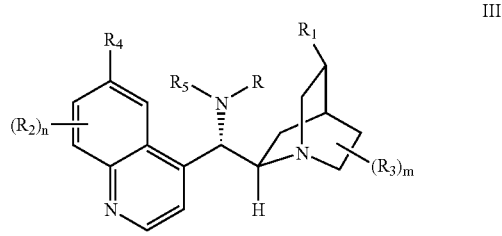

III wherein, independently for each occurrence:

R represents —C(=O)-aryl, —C(=O)-aralkyl, or —C(=O)-heterocyclic;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents lower alkyl;

n is an integer from 0 to 6 inclusive; and m is an integer from 0 to 8 inclusive.

16. A compound represented by formula IV:

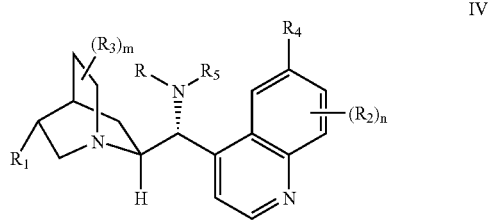

IV wherein, independently for each occurrence:

R represents C(=O)-aryl, —C(=O)-aralkyl, or —C(=O)-heterocyclic;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_5$ represents lower alkyl;

n is an integer from 0 to 6 inclusive; and m is an integer from 0 to 8 inclusive.

17. A method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

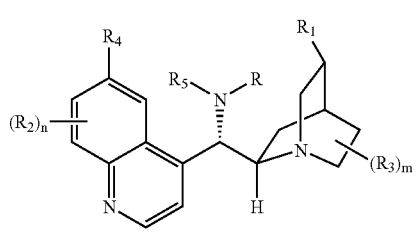

III wherein, independently for each occurrence:

R represents —C(=O)-aryl, —C(=O)-aralkyl, or —C(=O)-heterocyclic;

R$_1$ represents a substituted or unsubstituted alkyl or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_5$ represents lower alkyl;

n is an integer from 0 to 6 inclusive; and m is an integer from 0 to 8 inclusive.

18. A method of preparing a chiral, non-racemic β-cyano ketone, chiral, non-racemic β-keto ester, chiral, non-racemic β-cyano ester or chiral, non-racemic 1,3-diketone, comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

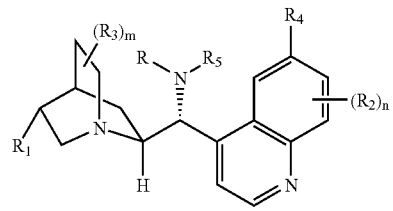

IV wherein, independently for each occurrence:

R represents —C(=O)-aryl, —C(=O)-aralkyl, or —C(=O)-heterocyclic;

R$_1$ represents a substituted or unsubstituted alkyl or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_5$ represents lower alkyl;

n is an integer from 0 to 6 inclusive; and m is an integer from 0 to 8 inclusive.

19. A method of kinetic resolution comprising the step of:

reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula III:

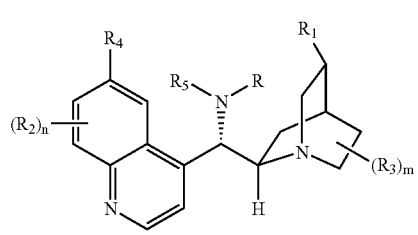

III wherein, independently for each occurrence:

R represents —C(=O)-aryl, —C(=O)-aralkyl, or —C(=O)-heterocyclic;

R$_1$ represents a substituted or unsubstituted alkyl or alkenyl;

R$_2$ and R$_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents lower alkyl;

n is an integer from 0 to 6 inclusive; and m is an integer from 0 to 8 inclusive.

20. A method of kinetic resolution comprising the step of:
reacting a prochiral β-cyano ketone, prochiral β-keto ester, prochiral β-cyano ester, or prochiral 1,3-diketone with an electron-deficient alkene in the presence of a catalyst; thereby producing a chiral, non-racemic β-cyano ketone, chiral, non-racemic β-keto ester, chiral, non-racemic β-cyano ester or chiral, non-racemic 1,3-diketone; wherein said catalyst is represented by formula IV:

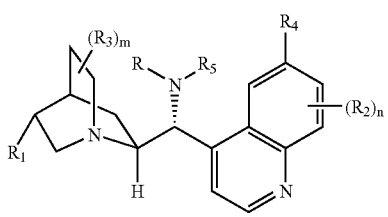

IV wherein, independently for each occurrence:

R represents C(=O)-aryl, —C(=O)-aralkyl, or —C(=O)-heterocyclic;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_4$ represents hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R_5$ represents lower alkyl;

n is an integer from 0 to 6 inclusive; and m is an integer from 0 to 8 inclusive.

* * * * *